Figure 1:
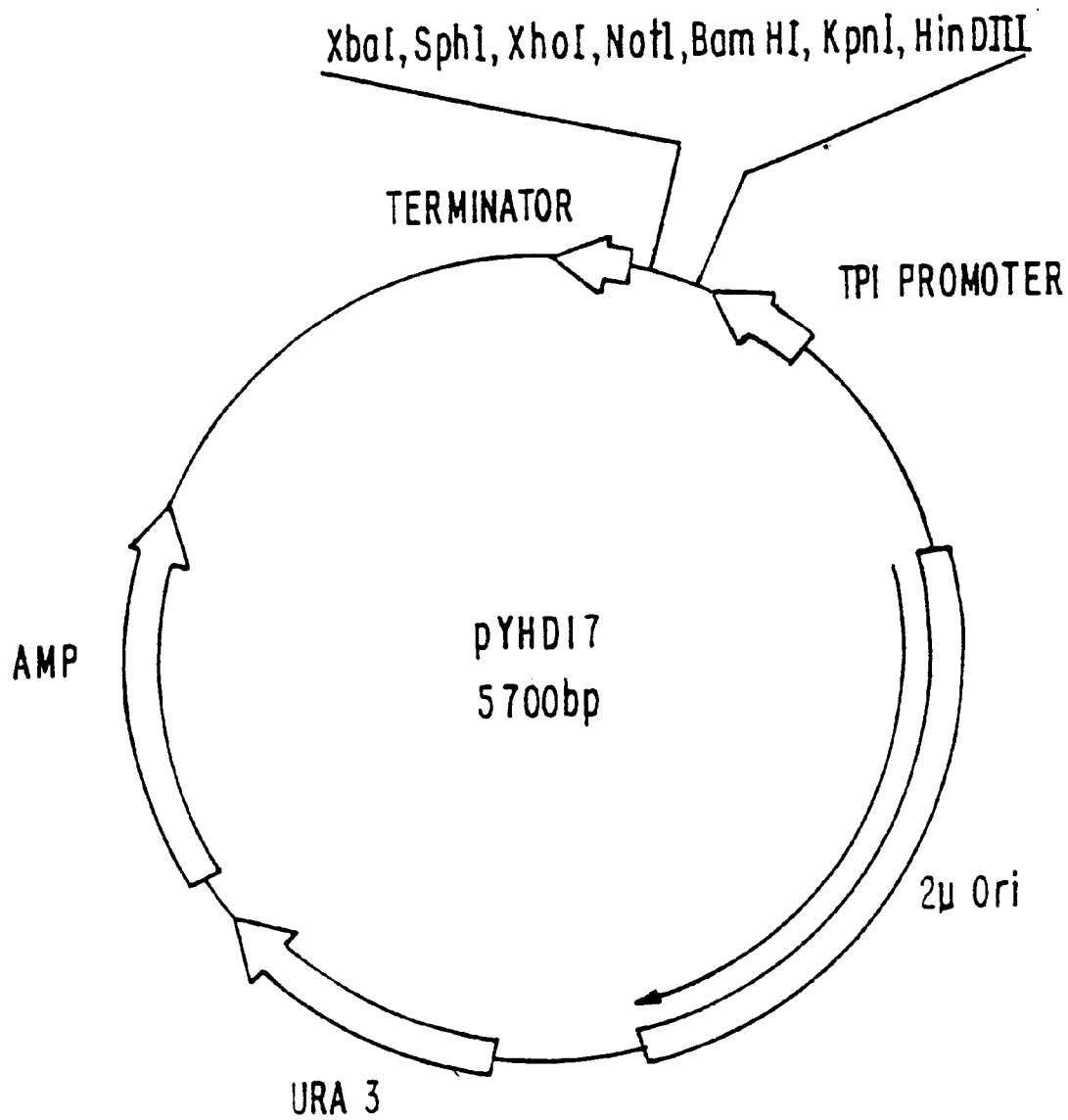

United States Patent [19]
Kofod et al.

[11] Patent Number: 6,033,900
[45] Date of Patent: Mar. 7, 2000

[54] ENZYME WITH RHAMNOGALACTURONASE ACTIVITY

[75] Inventors: Lene Venke Kofod, Uggerløse; Lene Nonboe Andersen, Birkerød; Henrik Dalbøge, Virum; Markus Sakari Kauppinen, Copenhagen; Stephan Christgau, Vedbæk; Hans Peter Heldt-Hansen, Virum; Claus Christophersen, Ringsted; Per Munk Nielsen, Hillerød, all of Denmark; Alphons Gerard Joseph Voragen; Hendrik Arie Schols, both of Wageningen, Netherlands

[73] Assignee: Novo Nordisk A/S, Bagsvaevd, Denmark

[21] Appl. No.: 09/201,505

[22] Filed: Nov. 30, 1998

Related U.S. Application Data

[62] Division of application No. 08/522,229, Sep. 25, 1995, Pat. No. 5,811,291, which is a continuation of application No. PCT/DK94/00097, Mar. 4, 1994.

[30] Foreign Application Priority Data

Mar. 5, 1993 [DK] Denmark .................................. 244/93

[51] Int. Cl.[7] .............................. C08B 30/04; C08B 1/00; C12N 9/24; A23B 7/10
[52] U.S. Cl. .......................... 435/275; 435/200; 435/208; 435/274; 435/262; 435/267; 426/44; 426/46; 426/49; 426/50; 426/52; 426/54
[58] Field of Search ..................................... 435/200, 208, 435/274, 275, 262, 267; 426/44, 46, 49, 50, 52, 54

[56] References Cited

U.S. PATENT DOCUMENTS 4,478,940  10/1984  Alder-Nissen et al. ................ 435/209

FOREIGN PATENT DOCUMENTS

WO 92/19728  11/1992  WIPO .

OTHER PUBLICATIONS

Schols et al., Carbohydrate Research, vol. 206, p. 105–115, 1990.

Mutter, M., et al., "Rhamnogalacturonan α–L–Rhamnopyranohydrolase", Plant Physiol. (1994) 106: 241–250.

Azadi, P. et al., "The backbone of the pectic polysaccharide rhamnogalacturonan 1 is cleaved by an endohydrolase and an endolyase", Glycobiology vol. 5, No. 8, pp. 783–789, 1995.

Kofod, L.V. et al., "Cloning and Characterization of Two Structurally and Functionally Divergent Rhamnogalacturonases from *Aspergillus aculeatus*", *The Journal of Biological Chemistry*, 1994, vol. 269, No. 46, issue of Nov. 18, pp. 29182–29189, 1994.

Mutter, M. et al., "Rhamnogalacturonase B from *Aspergillus aculeatus* ls a Rhamnogalacturonan α–L–Rhamnopyranosyl–(1–4)–α–D–Galactopyranosyluronide Lyase!", Plant Physiol./1996) 110:73–77.

*Primary Examiner*—Lisa J. Hobbs
*Assistant Examiner*—Einar Stole
*Attorney, Agent, or Firm*—Steve T. Zelson; Valeta Gregg

[57] ABSTRACT

Animal feed compositions and methods for treating one or more of soy, pea or rape-seed, or other material derived from Fabales or Cruciferaceae, with an enzyme having rhamnogalacturonase activity, wherein the enzyme having rhamnogalacturonase activity cleaves a rhamnogalacturonan backbone to produce rhamnose as a non-reducing end (RGase II) or cleaves a rhamnogalaturonan backbone to produce galacturonic acid as a non-reducing end.

14 Claims, 10 Drawing Sheets

ENZYME WITH RHAMNOGALACTURONASE ACTIVITY

CROSS-REFERENCE TO RELATED APPLICATIONS

This application is a divisional application of U.S. Ser. No. 08/522,229 filed Sep. 25, 1995, now U.S. Pat. No. 5,811,291, which is a continuation of PCT/DK94/00097, filed on Mar. 4, 1994, and claims priority under 35 U.S.C. 119 of Danish application 0244/93 filed Mar. 5, 1993, the contents of which are fully incorporated herein by reference.

FIELD OF INVENTION

The present invention relates an enzyme exhibiting rhamnogalacturonase activity, a DNA construct encoding the enzyme, an enzyme preparation comprising the enzyme, and the use of a rhamnogalacturonase for degradation or modification of plant cell materials.

BACKGROUND OF THE INVENTION

Plants contain rhamnogalacturonans, i.e. polysaccharides with more or less regularly alternating rhamnose and galacturonic acid residues in the backbone. The rhamnogalacturonans may have mono, oligo, and polysaccharide side-branches. Rhamnogalacturonans are part of the pectin-polymers, a major component of the plant cell walls.

Most pectin-polymers are composed of smooth regions, i.e. linear homogalacturonan, and hairy (ramified) regions. The hairy regions consist of a rhamnogalacturonan backbone with side-branches of varying length. The side-branches includes monosaccharides like xylose, galactose and arabinose, and oligo and polysaccharides like araban, galactan and arabinogalactan. Further the rhamnogalacturonan backbone is methylated and acetylated. The composition of the very complex structure of the hairy regions vary according to the source of the plant cell wall, cf Fry (1988), Schols et al. (1990b), O'Neill et al. (1990), Voragen and Schols (1992) and Carpita and Gibeaut (1993).

The enzymatic liquefaction and degradation of plant materials (e.g. fruits, vegetables, cereals, oil fruits and seeds) by technical processes involves combinations of pectolytic, cellulolytic and proteolytic enzyme preparations. However the hairy regions of pectin cause problems in such processes, because they are resistant to degradation of most technical enzyme preparations. A more extensive degradation of hairy regions is desired in many processes in order to improve the liquefaction and degradation of the plant material. For instance, an extensive degradation is important in processing of clear liquids and in processing of viscous plant cell wall containing material where a viscosity reduction is otherwise difficult to obtain. Furthermore, a more specific enzymatic degradation of the hairy regions is desirable for e.g. production of cloudy liquids, purification of pectin and soluble dietary fibres.

For these processes a degradation of the backbone of pectin hairy regions is of major importance. The degradation of the backbone of the hairy regions is performed by enzymes designated rhamnogalacturonases (RGases). RGases are believed to hydrolyse the bond between rhamnose and galacturonic acid. In order to facilitate the activity of RGases it may be desirable to reduce the degree of acetylation of the backbone, e.g. by use of the enzyme rhamnogalacturonan acetyl esterase (cf Searle-van Leeuwen et al., 1992). Furthermore, a reduced degree of branching of parts of the hairy regions may be desirable. The reduced degree of branching may be obtained by enzymes which attacks the side-branches, like galactanases, arabinanases, beta-galactosidases, alpha-arabinosidases and beta-xylosidases.

The isolation and purification of a RG'ase from *Aspergillus aculeatus* is described by Schols et al. (1990a).

WO 92/19728, the contents of which are incorporated by reference herein, discloses partial amino acid sequences of different RGases isolated from the Aspergllus sp. *A. aculeatus* and *A. japonicus* and from Irpex lacteus. EP 570 075 discloses an Aspergillus RGase gene and the construction of recombinant Aspergillus strains which overexpress RGase.

The RGase described by Schols et al., (1990a) has been found to have a similar degradation pattern to the *A. aculeatus* RGase described in WO 92/19728 and has been found to be immunologically cross-reactive with said RGase. RGase of this type is termed RGase II in the following disclosure.

Furthermore, in an article of Colquhoun (1990), the composition of a mixture of oligosaccharides obtained by enzymatic degradation of the modified hairy (ramified) regions of apple pectin with RGase II is described. It is shown that RGase II hydrolyses in the rhamnogalacturonan backbone leaving rhamnose as the non-reducing end in the degradation products.

Furthermore, RGase II type activity isolated from *Trametes sanguinea* on protopectin extracted from sugar beet has been reported recently by Sakamoto et al., 1993.

It has been shown that *A. aculeatus* RGase II exhibits optimum activity in the pH range of 3–4, which is lower than the pH of most plant materials and lower than desired pH in most industrial processes. The RGase disclosed in EP 570 075 and the *Trametes sanguinea* RGase mentioned above are stated to be used at pH 5.0.

High activity of RGase II has only been demonstrated on hairy regions from a limited number of plants, there is no reports of a significant activity of RGase II on hairy regions from soy and beets.

Especially for the industries dealing with modifications of plant cell walls for e.g. human nutrition and for animal feed (e.g. liquefaction of fruits, vegetables, cereals, oil fruits and seeds), it is important to provide a variety of different RGases (in respect to mode of action, pH and temperature range) in order to be able to exploit the desirable actions of RGases under widely varying technical process conditions. In particular there is a need for rhamnogalacturonase which is active at a higher pH than RGase II and which is active on plant materials for which RGase II has only limited activity.

BRIEF DISCLOSURE OF THE INVENTION

It has now surprisingly been found that a strain of *A. aculeatus* produces a second RGase which has a mode of action entirely different to that of the *A. aculeatus* RGase disclosed in WO 92/19728 and by Schols et al. (1990a).

Accordingly, in a first aspect the invention relates to an enzyme exhibiting RGase activity, which enzyme.

a) is encoded by the DNA sequence shown in SEQ ID No. 1 or a sequence homologous thereto encoding a polypeptide with RGase activity, b) has the amino acid sequence shown in SEQ ID No. 2 or an analogous sequence thereof, and/or c) is reactive with an antibody raised against the enzyme encoded by the DNA sequence shown in SEQ ID No. 1, d) has a pH optimum above pH 5, and/or e) has a relative activity of at least 30% at a pH in the range of 5.5–6.5.

In the following disclosure said enzyme is termed RGase I.

The pH optimum is determined as described in the Materials and Methods section herein. The relative activity is determined as described in the Materials and Methods section herein and is evaluated relative to activity at optimum pH. It will be understood that the pH optimum or relative activity as defined above is to be determined on an enzyme purified to homogeneity.

In a further aspect the invention relates to an enzyme exhibiting RGase activity, which enzyme is encoded by a DNA sequence comprising at least one of the following partial sequences

| | |
|---|---|
| (a) | CGTCGC TTCTGTCGTT |
| (b) | CGTGGCCTTC ACGGCCCAGGT |
| (c) | CGCCCACGCG GCCTTTGGCA |
| (d) | TCACCACCAG CTCCAGCGCC |
| (e) | TATGTCATCG ACACCAACGC |
| (f) | GCCAAACCAG CTGAAGTTCA |
| (g) | CCGTCAGCCG CAGCAGCTGC |
| (h) | ACATTACCTC CATCATCCAC |
| (i) | TATGGCACGG AGCTGCAGTA |
| (j) | CTCCAGCCAG GGCAGTCACA |
| (k) | TTGGGTCGGG TCTGGGCTCT |

In a still further aspect the invention relates to an enzyme exhibiting RGase activity, which is encoded by a DNA sequence comprising the following partial DNA sequence.

CGTCGC TTCTGTCGTT CGTGGCCTTC ACGGCCAGGT CGCCCACGCG GCCTTTGGCA TCACCACCAG CTCCAGCGCC TATGTCATCG ACACCAACGC GCCAAACCAG CTGAAGTTCA CCGTCAGCCG CAGCAGCTGC GACATTACCTC CATCATCCAC TATGGCACGG AGCTGCAGTA CTCCAGCCAG GGCAGTCACA TTGGGTCGGG TCTGGGCTCT or a sequence homologous thereto encoding a polypeptide with RGase activity.

In the present context the term "RGase activity" is intended to indicate that the enzyme exhibits depolymerization activity of pectin hairy regions by attacking the rhamnogalacturonan backbone. The depolymerization of the pectin hairy region can be demonstrated by gel filtration chromatography as described below. The pectin hairy regions may be prepared from apples by purification and deacetylation as described in Schols et al (1990a,b). The degradation of possible polygalacturonic parts present in the material is ensured by further degradation with Pectinex 3X (obtainable from Novo Nordisk) and recovery of the deacetylated hairy regions by ultrafiltration.

In the present context, the term "homologue" is intended to indicate a polypeptide encoded by DNA which hybridizes to the same probe as the DNA coding for the RGase enzyme under certain specified conditions (such as presoaking in 5×SSC and prehybridizing for 1 h at −40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labelled probe for 18 h at −40° C. followed by washing three times in 2×SSC, 0.2% SDS at 40° C. for 30 minutes). More specifically, the term is intended to refer to a DNA sequence which is at least 70% homologous to the sequence shown above encoding the RGase 1 of the invention, such as at least 75%, at least 80%, at least 85%, at least 90% or even at least 95% homologous to any of the sequences shown above. The term is intended to include modifications of the DNA sequence shown above, such as nucleotide substitutions which do not give rise to another amino acid sequence of the RGase but which correspond to the codon usage of the host organism into which the DNA construct is introduced or nucleotide substitutions which do give rise to a different amino acid sequence and therefore, possibly, a different protein structure which might give rise to a RGase mutant with different properties than the native enzyme. Other examples of possible modifications are insertion of one or more codons into the sequence, addition of one or more codons at either end of the sequence, or deletion of one or more codons at either end or within the sequence.

In the present context, the term "analogous sequence" is intended to indicate an amino acid sequence differing from that of SEQ ID No. 2 respectively, by one or more amino acid residues. The analogous sequence may be one resulting from modification of the amino acid sequence shown in the SEQ ID, e.g. involving substitution of one or more amino acid residues at one or more different sites in the amino acid sequence, deletion of one or more amino acid residues at either or both ends of the enzyme or at one or more sites in the amino acid sequence, or insertion of one or more amino acid residues at one or more sites in the amino acid sequence. The modification of the amino acid sequence may suitably be performed by modifying the DNA sequence encoding the enzyme, e.g. by site-directed or by random mutagenesis or a combination of these techniques in accordance with well-known procedures. Alternatively, the analogous sequence may be one of an enzyme derived from another origin than the RGase corresponding to SEQ ID No. 2. The analogous sequence will normally exhibit a degree of homology (in terms of identity) of at least 70%, such as at least 75%, 80%, 85%, 90% or even 95% with the amino acid sequence shown in SEQ ID No. 2.

In a further aspect the invention relates to a DNA construct encoding the RGase of the invention, an expression vector comprising the DNA construct and a host cell comprising the vector or the DNA construct.

In final aspects, the invention relates to the use of an enzyme exhibiting RGase activity for reduction of the viscosity of a plant cell wall material, for extraction of high molecular weight material from a plant cell wall material or for degradation or modification of a plant cell wall material at a pH in the range of 4–8, as well as to methods for obtaining such effects by use of an enzyme exhibiting RGase activity.

As far as the present inventors are aware the use of RGase for these purposes has neither been disclosed nor suggested in any prior art reference.

DETAILED DISCLOSURE OF THE INVENTION

It has surprisingly been found that the RGase comprising the amino acid sequence shown in SEQ ID No. 2 cleaves a rhamnogalacturonan backbone in another manner than the prior art RGases. More specifically, it has been found that the RGase cleaves a rhamnogalacturonan backbone in such a manner that galacturonic acids are left as the non-reducing ends in the degradation products. As far as the present inventors are aware no prior disclosure exists of an RGase having this type of cleavage capabilities.

Furthermore, it has been found the RGase of the invention exhibits activity on hairy regions from a soy bean material. As far as the present inventors are aware RGase activity on soy bean material has never been reported. In addition it has been found that RGase I of the invention exhibits activity on saponified hairy regions from a sugar beet material.

On the basis of the above observations it is contemplated that RGases disclosed herein are members of an entirely new class of RGases. Accordingly, in a further aspect the invention relates to a RGase enzyme which.

i) cleaves a rhamnogalacturonan backbone in such a manner that galacturonic acids are left as the non-reducing ends, ii) exhibits activity on hairy regions from a soy bean material, and/or iii) exhibits activity on saponified hairy regions from a sugar beet material.

The enzyme of the invention is preferably derivable from a strain of Aspergillus sp. in particular *A. aculeatus* or *A. japonicus*, a strain of Irpex sp., e.g. *I. lacteus*, or a strain of Trichoderma sp., Neurospora sp., Penicillium sp., Trametes sp. or Polyporus sp.

In the present context, the term "derivable from" is intended not only to indicate a RGase produced by a strain of the above mentioned fungi, but also a RGase encoded by a DNA sequence isolated from strain of *A. aculeatus* and produced in a host organism transformed with said DNA sequence.

In particular the enzyme of the invention may be encoded by a DNA sequence isolated from a DNA library of *A. aculeatus*, CBS 101.43.

The DNA construct of the invention may be isolated by a general method involving.

cloning, in suitable vectors, a DNA library from *Aspergillus aculeatus*, transforming suitable yeast host cells with said vectors, culturing the host cells under suitable conditions to express any enzyme of interest encoded by a clone in the DNA library, and screening for positive clones by determining any RGase activity of the enzyme produced by such clones, the RGase activity being determined by use of coloured crosslinked substrates containing the rhamnogalacturonan backbone of the pectin hairy regions such as AZCL-arabinan, AZCL-galactan or a coloured and crosslinked MHR-substrate as described below in the section entitled "Materials and Methods".

The AZCL-arabinan and AZCL-galactan substrates can be used as screening substrates for RGases since the present inventors discovered that these arabinan and galactan substrates are hairy regions in which the galactan and arabinan are linked as side branches to a rhamnogalacturonan backbone. Enzymatic hydrolysis of the backbone leads to a depolymerization of the AZCL-substrate and consequently to a release of the colour. Activity by galactanases and arabinanases, respectively, will also lead to a colour release from such AZCL-substrates. The RGase of the invention was initially isolated on both AZCL-galactan and AZCL-arabinan and coloured cross-linked hairy regions from apples. In the priority establishing application this enzyme was designated as "Carbohydrase" due to the activity on the different types of carbohydrate substrates. The subsequent studies of the enzyme revealed that it was a RGase, and this term is, accordingly, used throughout the present application.

A more detailed description of this screening method is given in Example 1 below.

The DNA sequence coding for the RGase enzyme may for instance be isolated by screening a cDNA library of *Aspergillus aculeatus*, e.g strain CBS 101.43, publicly available from the Centraalbureau voor Schimmelcultures, Delft, NL, and selecting for clones expressing RGase activity. The appropriate DNA sequence may then be isolated from the clone by standard procedures, e.g. as described in Example 1.

The DNA sequence may subsequently be inserted into a recombinant expression vector. This may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding the RGase should be operably connected to a suitable promoter and terminator sequence. The promoter may be any DNA sequence which shows transcriptional activity in the host cell of choice and may be derived from genes encoding proteins either homologous or heterologous to the host cell. The procedures used to ligate the DNA sequences coding for the RGase, the promoter and the terminator, respectively, and to insert them into suitable vectors are well known to persons skilled in the art (cf., for instance, Sambrook et al., *Molecular Cloning. A Laboratory Manual*, Cold Spring Harbor, N.Y., 1989).

The host cell which is transformed with the DNA sequence of the invention is preferably a eukaryotic cell, in particular a fungal cell such as a yeast or filamentous fungal cell. In particular, the cell may belong to a species of Aspergillus, most preferably *Aspergillus oryzae* or *Aspergillus niger*. Fungal cells may be transformed by a process involving protoplast formation and transformation of the protoplasts followed by regeneration of the cell wall in a manner known per se. The use of Aspergillus as a host microorganism is described in EP 238 023 (of Novo Nordisk A/S), the contents of which are hereby incorporated by reference. The host cell may also be a yeast cell, e.g. a strain of Saccharomyces, in particular *Saccharomyces cerevisiae*.

In a still further aspect, the present invention relates to a method of producing an RGase enzyme, wherein a suitable host cell transformed with a DNA sequence encoding the enzyme is cultured under conditions permitting the production of the enzyme, and the resulting enzyme is recovered from the culture.

The medium used to culture the transformed host cells may be any conventional medium suitable for growing the host cells in question. The expressed RGase may conveniently be secreted into the culture medium and may be recovered therefrom by well-known procedures including separating the cells from the medium by centrifugation or filtration, precipitating proteinaceous components of the medium by means of a salt such as ammonium sulphate, followed by chromatographic procedures such as ion exchange chromatography, affinity chromatography, or the like.

The thus purified RGase may be employed for immunization of animals for the production of antibodies. More specifically, antiserum against the RGase of the invention may be raised by immunizing rabbits (or other rodents) according to the procedure described by N. Axelsen et al. in: *A Manual of Ouantitative Immunoelectrophoresis*, Blackwell Scientific Publications, 1973, Chapter 23, or A. Johnstone and R. Thorpe, *Immunochemistry in Practice*, Blackwell Scientific Publications, 1982 (more specifically pp. 27–31). Purified immunoglobulins may be obtained from the antisera, for example by salt precipitation (($NH_4)_2SO_4$), followed by dialysis and ion exchange chromatography, e.g. on DEAE-Sephadex. Immunochemical characterization of proteins may be done either by Outcherlony double-diffusion analysis (O. Ouchterlony in: *Handbook of Experimental Immunology* (D. M. Weir, Ed.), Blackwell Scientific Publications, 1967, pp. 655–706), by crossed immunoelectrophoresis (N. Axelsen et al., supra, Chapters 3 and 4), or by rocket immunoelectrophoresis (N. Axelsen et al., Chapter 2,).

The Enzyme Preparation of the Invention

In a still further aspect, the present invention relates to an enzyme preparation useful for the degradation of plant cell wall components, said preparation being enriched in an enzyme exhibiting RGase I activity as described above. In this manner a boosting of the cell wall degrading ability of the enzyme preparation can be obtained.

The enzyme preparation having been enriched with an enzyme of the invention may e.g. be an enzyme preparation comprising multiple enzymatic activities, in particular an enzyme preparation comprising multiple plant cell wall degrading enzymes such as Pectinex®, Pectinex Ultra SP®, Celluclast or Celluzyme (all available from Novo Nordisk A/S). In the present context, the term "enriched" is intended to indicate that the RGase I activity of the enzyme preparation has been increased, e.g. with an enrichment factor of at least 1.1, conveniently due to addition of an enzyme of the invention prepared by the method described above.

Alternatively, the enzyme preparation enriched in an enzyme exhibiting RGase I activity may be one which comprises an enzyme of the invention as the major enzymatic component, e.g. a mono-component enzyme preparation.

The enzyme preparation may be prepared in accordance with methods known in the art and may be in the form of a liquid or a dry preparation. For instance, the enzyme preparation may be in the form of a granulate or a microgranulate. The enzyme to be included in the preparation may be stabilized in accordance with methods known in the art.

The enzyme preparation of the invention may, in addition to a RGase I of the invention, contain one or more other plant cell wall degrading enzymes, for instance those with proteolytic, cellulytic, xylanolytic or pectinolytic activities such as, xylanase, arabinanase, RGase, e.g. RGase II, pectin acetyl esterase, galactanase, polygalacturonase, pectin lyase, pectate lyase, glucanase, rhamnogalacturonan acetyl esterase or pectin methylesterase. The preparation may further contain one or more enzymes exhibiting exo-activity on the same substrates as the above-mentioned endo-enzymes, like α-arabinosidase, β-galactosidase and β-xylosidase. The additional enzyme(s) may be producible by means of a microorganism belonging to the genus Aspergillus, preferably *Aspergillus niger, Aspergillus aculeatus, Aspergillus awamori* or *Aspergillus oryzae*, Penicillium or Trichoderma.

Uses of RGase

In the following various uses of an enzyme of the invention or of RGase in general are described.

An important use of the enzyme or enzyme preparation of the invention or any enzyme exhibiting RGase activity in the pH range of 4–8 is in the degradation or modification of plant cell wall containing material which is to be performed at a pH in the range of 4–8, preferably 4.5–7.5, such as 5.0–7.5, 5.2–7.3 or 5.5–7 and most preferably in the range of 5.5–6.5. It has surprisingly been found that the enzyme according to the invention is active under conditions where the RGase II described in the prior art has no or little activity. The activity at these pH values is advantagous for processing of many types fruits and vegetable where the pH may be to high for optimal use of RGase II. This may apply, e.g. to the processing of rape seeds, carrots, tomatoes, potatoes, olives, soy and sugar beets.

The enzyme and enzyme preparation of the invention is preferably used at a temperature in the range of 15–65° C., preferably 20–60° C., more preferably 25–55° C. and most preferably in the range of 35–40° C.

Another important use of the enzyme or the enzyme preparation of the invention or any enzyme with RGase activity is in the degradation of plant cell wall containing material, in particular plant cell wall material originating from plants belonging to Fabales (Leguminales), preferably soya, peas, bean, locust bean and guar, or to the family Cruciferaceae, such as rape seed or cabbage. It has surprisingly been demonstrated that the enzyme according to the invention has a significant activity on cell wall material including hairy regions of these types of plants, and it is contemplated that any RGase may exhibit activity on such plants. The activity may be obtained without any deacetylation of the hairy regions.

The use of RGases on cell wall containing materials from the members of the order Fabales or the family Cruciferaceae is advantageous in that an increased digestibility of, e.g., soya, pea and rape seed may be obtained. Furthermore, processing of these materials may be facilitated by use of RGase. For instance, the use of RGase may facilitate the purification of soya protein and soya isolate or facilitate the processing of soy material to be used for animal feed or human food. Furthermore, the use is advantageous for the release of high molecular weight material from this type of plant material (such as soy beans, peas or rapeseeds). For instance, RGase may be used to release galactan-rich material from soy beans. This material can be used as soluble fibres to be added to different types of food in order to improve the nutritional value thereof.

Furthermore, the RGase of the invention have been found to exhibit acitivity on plants belonging to the order Chenopodiaceae, such as beets, sugar beets, red beets and spinach.

The use of RGases on cell wall containing material from plant belonging to the Chenopodiaceae is advantagous for processing of sugar beets e.g. liquefaction of sugar beets for production of ethanol and recovery of galacturonic acid, or for processing of sugar beet pulp for recovery of pectin, recovery of galacturonic acid, or to improve the pressability of the beet pulp. Further the RGases may be used to improve the recovery of the colour from red beets. The RGase may be used alone or in combination with other enzymes, such as a rhamnogalacturonan acetyl esterase.

Another important use of the enzyme and enzyme preparation of the invention or any enzyme with RGase activity is in reducing the viscosity of a plant material. For instance, the viscosity reduction may be used to facilitate processing of the plant material or the separation of the plant material into different components. The viscosity reduction may also be used to improve the digestibility of a plant material. Specific examples include improving the purification of protein from e.g. soy beans, peas or rapeseeds, and improving the digestibility of soy based animal feed. It has surprisingly been demonstrated that the enzyme according to the invention can reduce the viscosity in jet cooked soy without addition of any other polysaccharide degrading enzymes.

By use of the method of the invention viscosity reductions of at least 20%, such as at least 30% and preferably at least 50% may be obtained.

Another important use of the enzyme or enzyme preparation of the invention is for extracting high molecular weight molecules from a plant cell wall material. In the present context, the term "high molecular weight molecules" is intended to indicate molecules having a degree of polymerization (DP) of at least 50 as defined herein. The enzyme is especially useful for extraction of pectin material which would otherwise be difficult to extract. For instance, the enzyme or enzyme preparation may be used to extract galactan and arabinan containing oligomers and polysaccharides, e.g. from soy fibres as described in the following examples. For this purpose the RGase of the invention may be used alone or in combination with another enzyme, such as with rhamnogalacturonan acetyl esterase.

By use of a RGase for such extraction it is possible to obtain high molecular weight polysaccharides having a DP of at least such as at least 500 or at least 1000.

Furthermore, the enzyme or enzyme preparation can be used to facilitate the extraction of pectin from, e.g., citrus, apples, beet or sunflower material. For this purpose it may be advantageous to use the enzyme alone or substantially free from polygalacturonase, pectin lyase or other enzymes which may depolymerize the pectin to be produced.

From the above disclosure, it will be apparent that it may be advantageous to use the RGase of the invention in combination with another plant cell wall degrading enzyme, e.g. of the type disclosed above.

Methods of the Invention

In further aspects the invention relates to methods of using a RGase, preferably in the form of an enzyme or enzyme preparation of the invention, for the above described uses. In the following these methods are summarized. It will be understood that the information provided in the above section ("Use of RGase) will also be applicable for the methods described in the present section.

The invention relates to a method of reducing the viscosity of a plant material, which method comprises treating the plant material with a enzyme or enzyme preparation of the invention under suitable conditions for the viscosity to be reduced. The pH and temperature under which the treatment is performed is typically as defined above.

By use of the method of the invention viscosity reductions of at least 20%, such as at least 30% and preferably at least 50% may be obtained.

The invention relates to a method of producing high molecular weight molecules having a DP of at least 50 from a plant material, which method comprises treating the plant material with an enzyme or enzyme preparation according to the invention under suitable conditions for the viscosity to be reduced. The pH and temperature under which the treatment is performed is typically as defined above.

Any of the plant materials specified above may be treated by the methods of the invention.

In a particularly important aspect the invention relates to a soy treatment process.

The production of soy isolates includes:

aqueous extraction for defatted soy flakes in mildly alkaline media, separation of the soluble protein from undissolved material, precipitation of protein by acid, separation of protein from soluble carbohydrates, neutralization of the precipitated protein, drying of protein, cf Circle et al., 1978.

It is characteristic for this process that the first extraction step is troublesome due to the water binding ability of the carbohydrate fraction which results in a high viscosity. This limits the yield and the production capacity of the separation equipment. It is contemplated that the first extraction step may be considerably improved by use of an RGase of the invention whereby a higher yield and a higher capacity of the entire process can be obtained.

Accordingly, in a further important aspect the invention relates to a method of producing a soy isolate, which method comprises treating a suspension of a defatted soy flour with a sufficient amount of an RGase to reducing the viscosity of the suspension, and isolating a soy isolate from the resulting suspension.

In this manner the suspension will be significantly easier to handle during processing for soy protein isolation. The processing of the suspension typically includes the steps of i) extracting protein by aqueous extraction at near neutral or slightly alkaline pH, ii) separating protein from undissolved material, iii) precipitating protein by acid precipitation, iv) separating precipitated protein from soluble material, and v) neutralizing and drying the protein.

Feed

The present invention relates to a feed comprising RGase, in particular in the form of an enzyme or enzyme preparation of the invention. The RGase is contemplated to reduce the viscosity of the feed by modifying components of the feed, i.e. in vitro, or in vivo. The RGase is particularly suited for addition to animal feed compositions containing soy, pea or rapeseed, or other material derived from Fabales or Cruciferaceae.

BRIEF DESCRIPTION OF THE INVENTION

The invention is further described in the accompanying drawing in which

Figure 2:
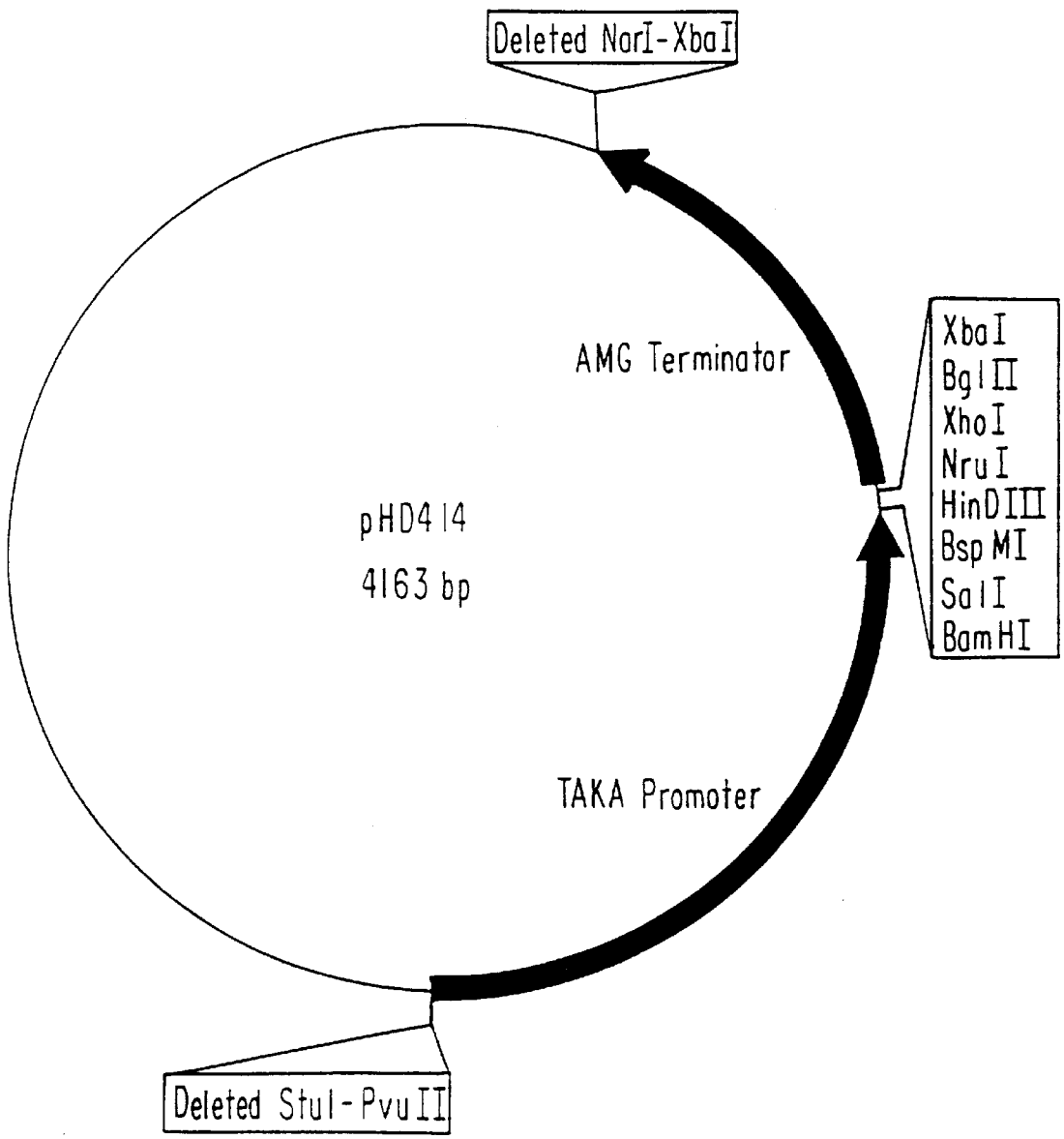
Figure 3:
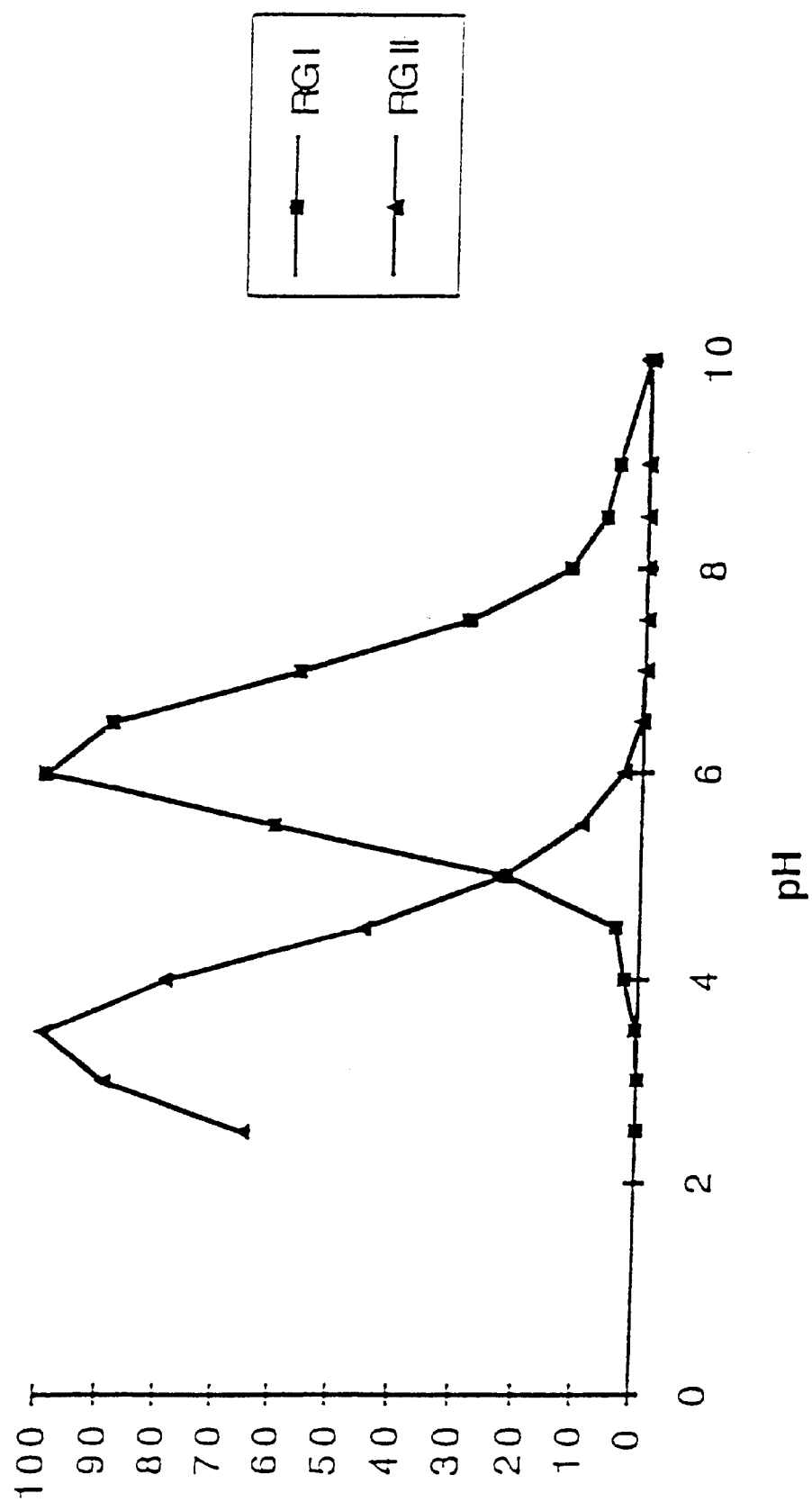
Figure 4:
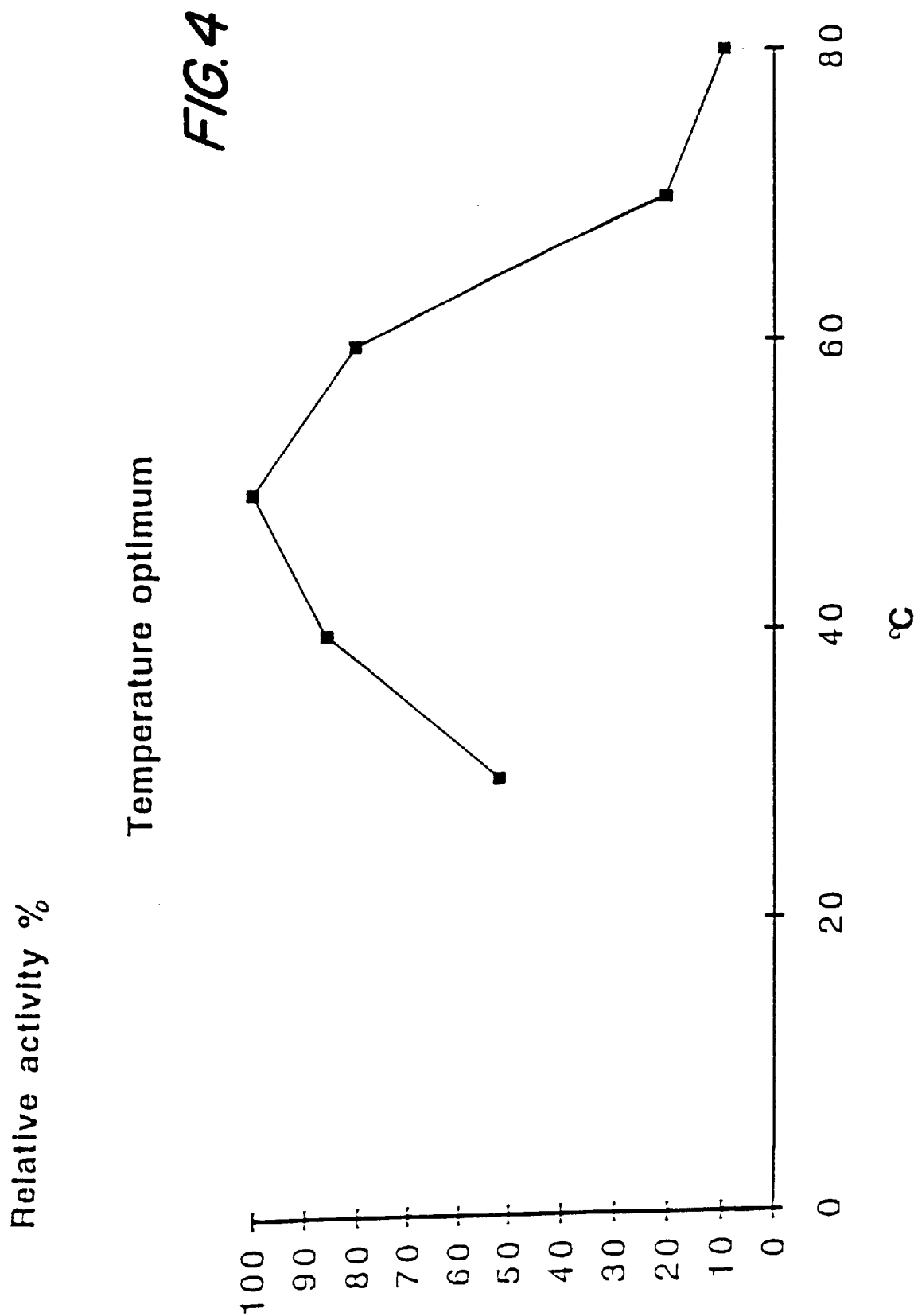
Figure 5:
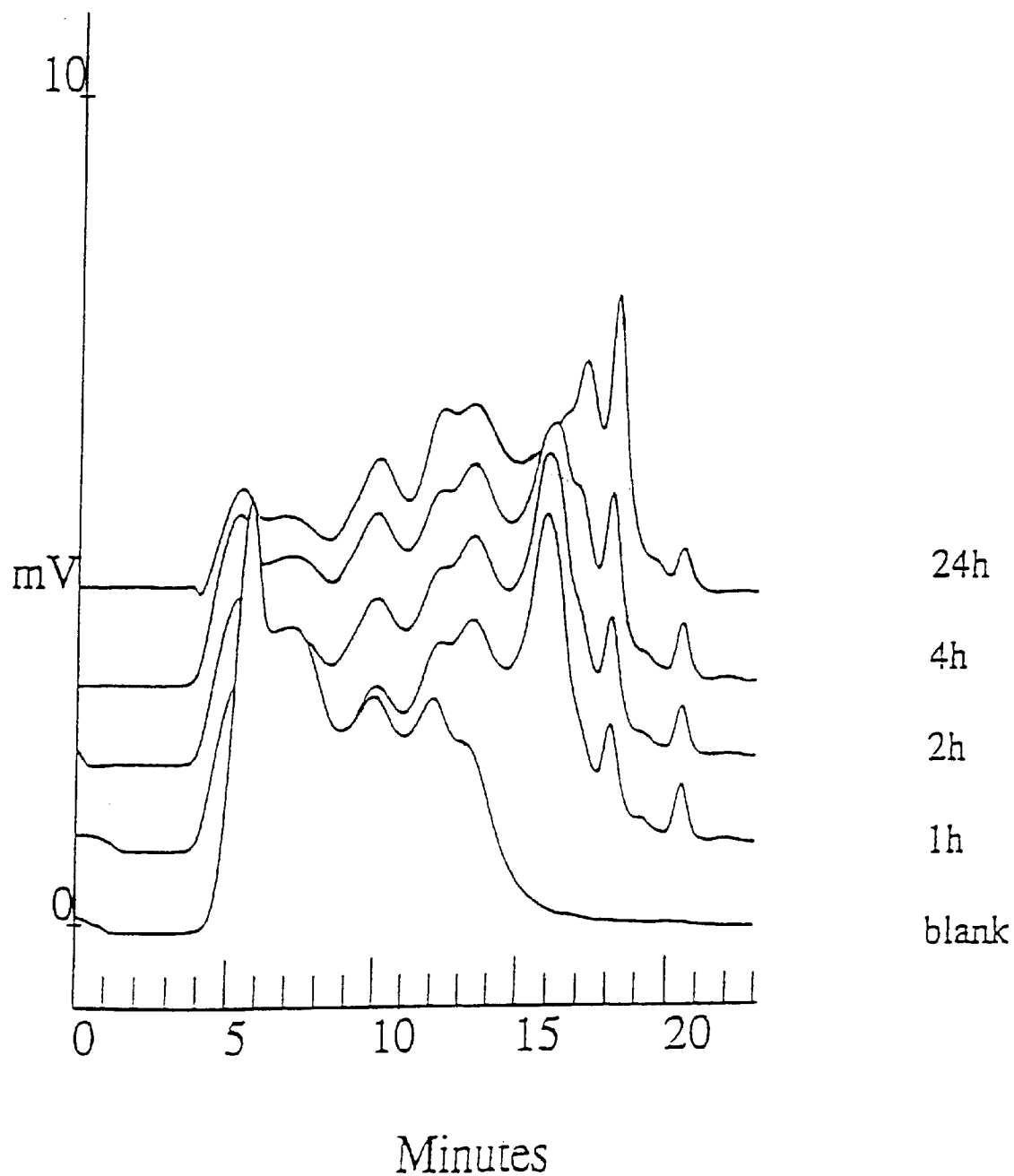

FIG. 1 is a restriction map of plasmid pYHD17,

FIG. 2 a restriction map of plasmid pHD 414,

FIG. 3 the pH optimums for RGase I and RGase II,

FIG. 4 the temperature optimum for RGase I,

FIG. 5 the SEC degradation pattern obtained on MHR-S by RGase I

Figure 6:
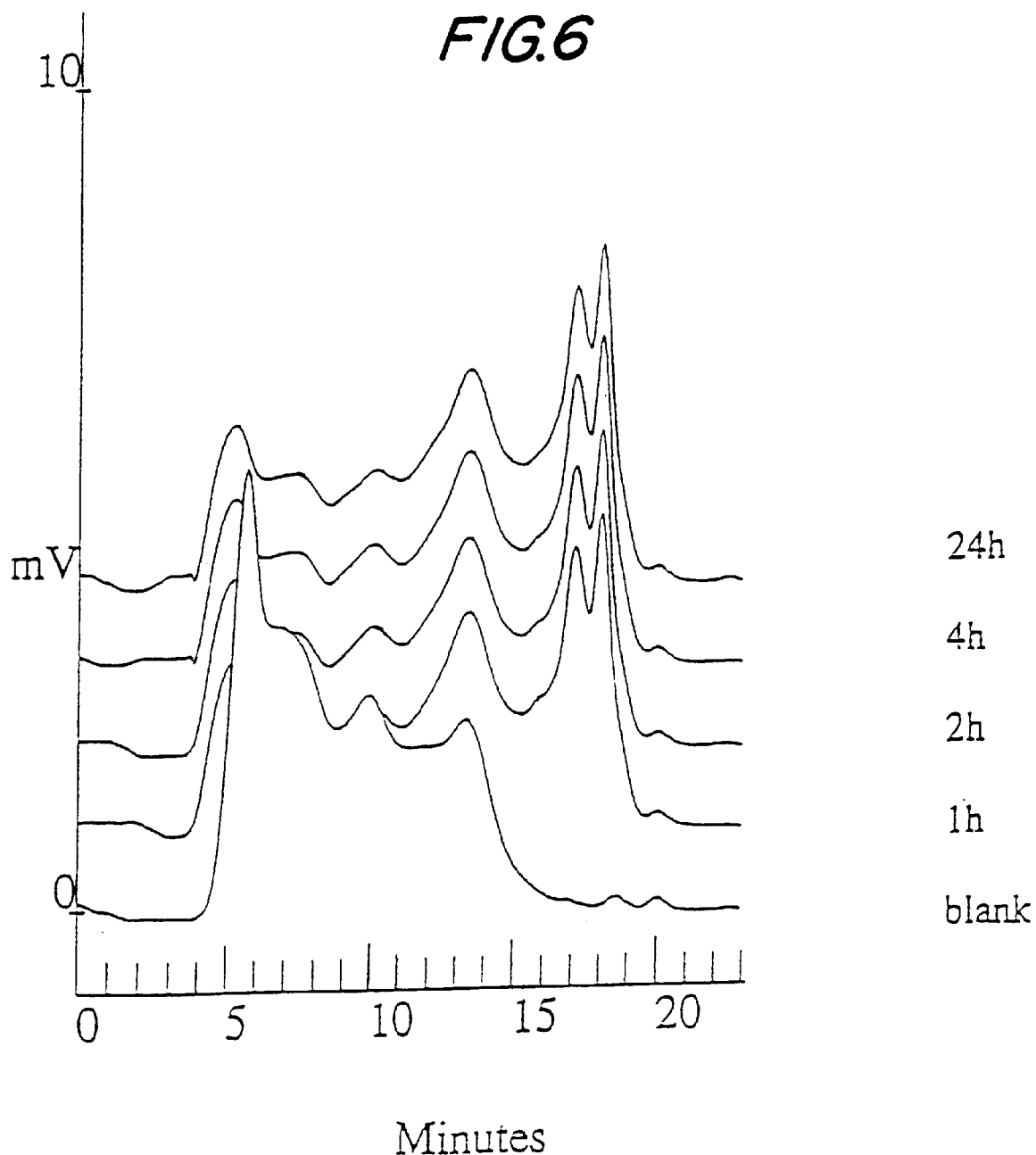
Figure 7:
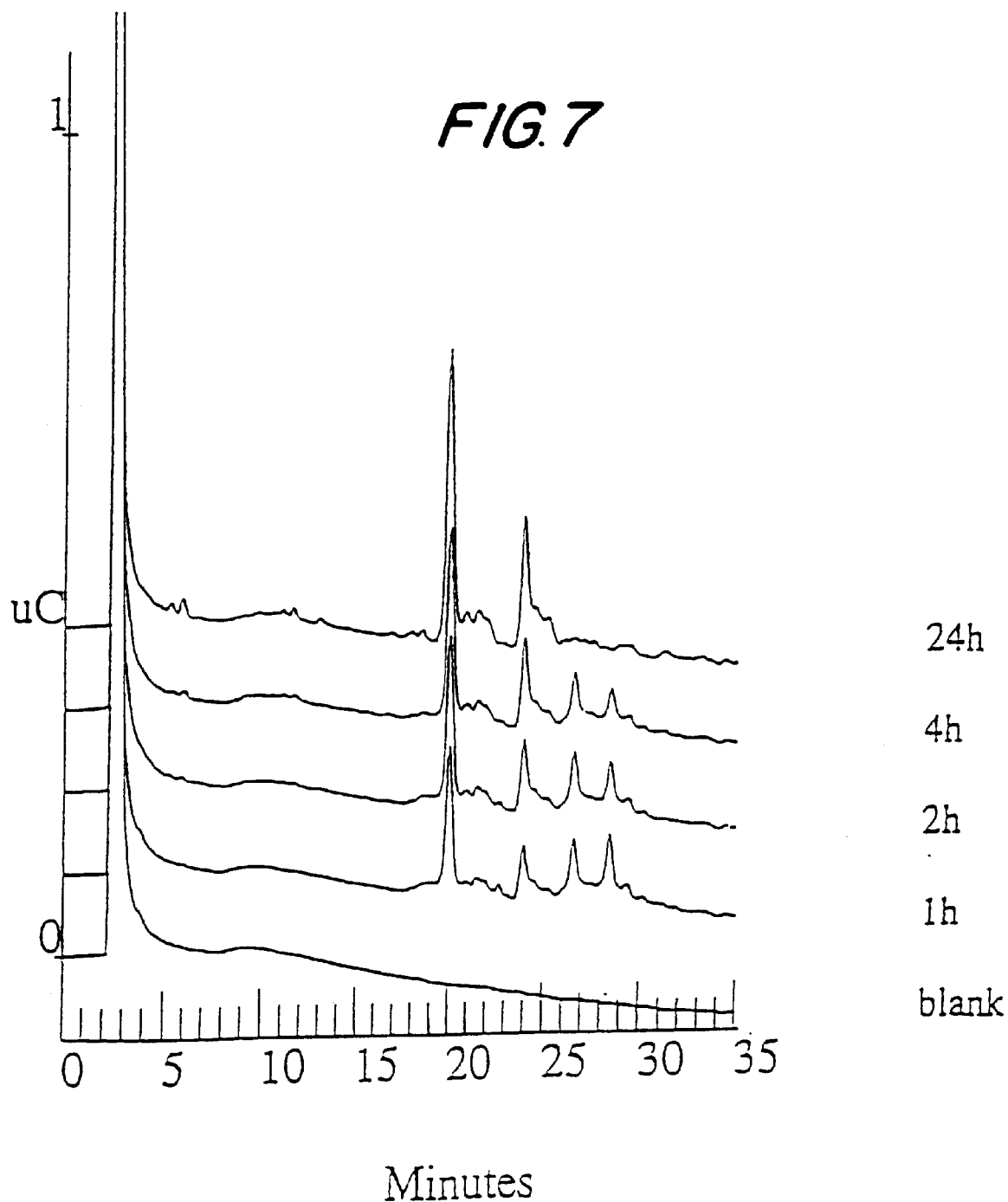
Figure 8:
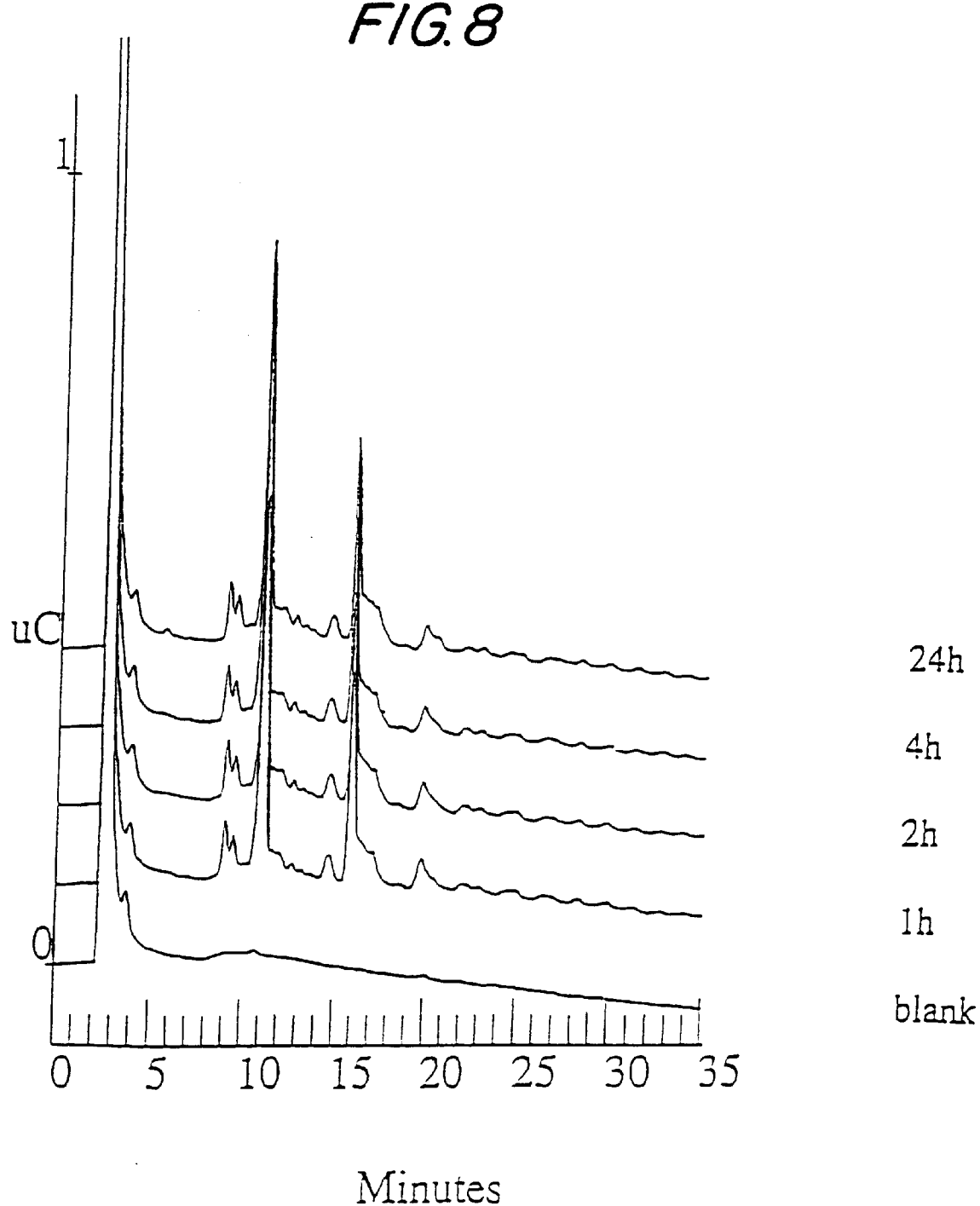
Figure 9:
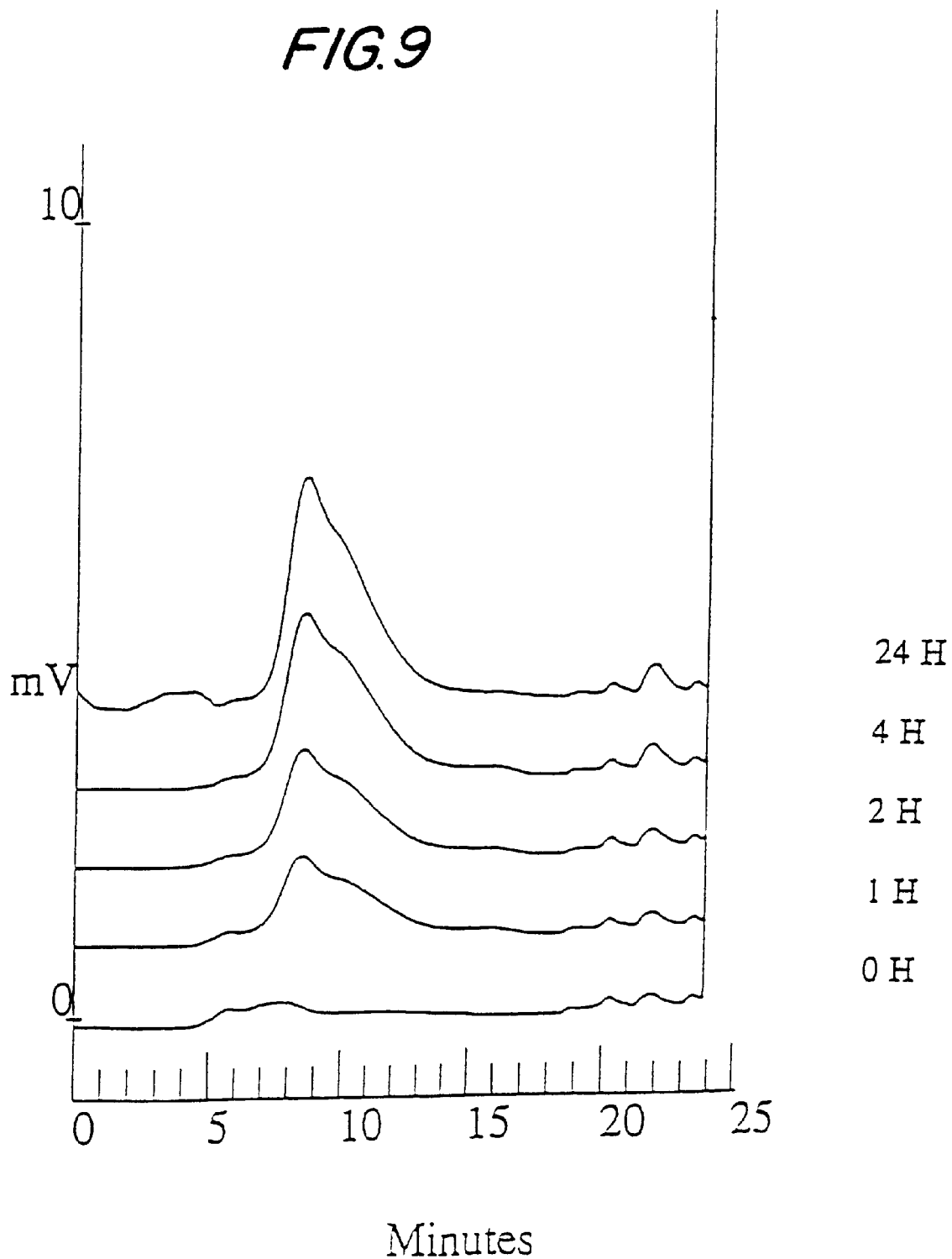
Figure 10:
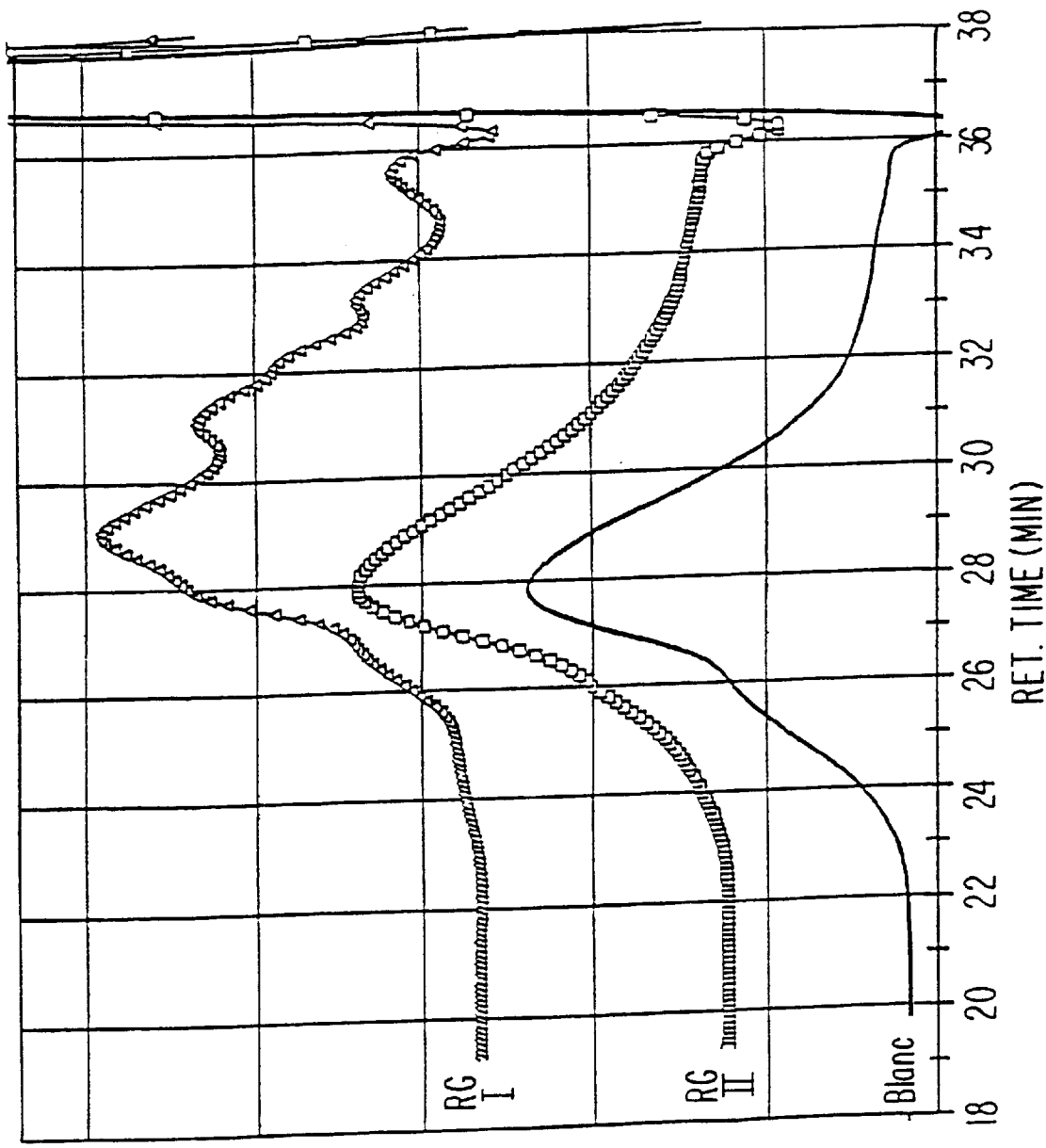

FIG. 6 the SEC degradation pattern obtained on MHR-S by RGase II,

FIG. 7 the result of anion exchange chromatography (HPAEC) of MHR-S degradation products obtained by RGase I, FIG. 8 the result of HPAEC of MHR-S degradation products obtained by RGase II, FIG. 9 the SEC of soluble polysaccharides obtained from 1% soy remanens treated with RGase I, FIG. 10 the degradation pattern obtained on beet modified hairy regions with RGase I and RGase II.

The invention is described in further detail in the following examples which are not in any way intended to limit the scope of the invention as claimed.

EXAMPLES

Materials and Methods

Donor organism: mRNA was isolated from *Aspergillus aculeatus*, CBS 101.43, grown in a soy-containing fermentation medium with agitation to ensure sufficient aeration. Mycelia were harvested after 3–5 days' growth, immediately frozen in liquid nitrogen and stored at −80° C.

Yeast strains: The *Saccharomyces cerevisiae* strain used was yNG231 (MAT alpha, leu2, ura3–52, his4–539, pep4-delta 1, cir+) or JG169 (MATα; ura 3–52; leu 2–3, 112; his 3-D200; pep 4–113; prc1::HIS3; prb1:: LEU2; cir+).

Construction of an expression plasmid: The commercially available plasmid pYES II (Invitrogen) was cut with SpeI, filled in with Klenow DNA polymerase+dNTP and cut with ClaI. The DNA was size fractionated on an agarose gel, and a fragment of about 2000 bp was purified by electroelution. The same plasmid was cut with ClaI/PvuII, and a fragment of about 3400 bp was purified by electroelution. The two fragments were ligated to a blunt-ended SphI/EcoRI fragment containing the yeast TPI promoter. This fragment was isolated from a plasmid in which the TPI promoter from *S. cerevisiae* (cf. T. Albers and G. Kawasaki, *J. Mol. Appl. Genet.* 1, 1982, pp. 419–434) was slightly modified: an internal SphI site was removed by deleting the four bp constituting the core of this site. Furthermore, redundant sequences upstream of the promoter were removed by Bal1 exonuclease treatment followed by addition of a SphI linker. Finally, an EcoRI linker was added at position −10. After these modifications, the promoter is included in a SphIEcoRI fragment. Its efficiency compared to the original promoter appears to be unaffected by the modifications. The resulting plasmid pYHD17 is shown in FIG. 1.

Preparation of RNase-free glassware, tips and solutions: All glassware used in RNA isolations was baked at +220° C. for at least 12 h. Eppendorf tubes, pipet tips and plastic columns were treated in 0.1% diethylpyrocarbonate (DEPC) in EtOH for 12 h, and autoclaved. All buffers and water (except Tris-containing buffers) were treated with 0.1% DEPC for 12 h at 37° C., and autoclaved.

Extraction of total RNA: The total RNA was prepared by extraction with guanidinium thiocyanate followed by ultracentrifugation through a 5.7 M CsCl cushion (Chirgwin et al., 1979) using the following modifications. The frozen mycelia were ground in liquid $N_2$ to fine powder with a mortar and a pestle, followed by grinding in a precooled coffee mill, and immediately suspended in 5 vols of RNA extraction buffer (4 M GuSCN, 0.5% Nalaurylsarcosine, 25 mM Na-citrate, pH 7.0, 0.1 M β-mercaptoethanol). The mixture was stirred for 30 min. at RT° and centrifuged (30 min., 5000 rpm, RT°, Heraeus Megafuge 1.0 R) to pellet the cell debris. The supernatant was collected, carefully layered onto a 5.7 M CsCl cushion (5.7 M CsCl, 0.1 M EDTA, pH 7.5, 0.1% DEPC; autoclaved prior to use) using 26.5 ml supernatant per 12.0 ml CsCl cushion, and centrifuged to obtain the total RNA (Beckman, SW 28 rotor, 25 000 rpm, RT°, 24h). After centrifugation the supernatant was carefully removed and the bottom of the tube containing the RNA pellet was cut off and rinsed with 70% EtOH. The total RNA pellet was transferred into an Eppendorf tube, suspended in 500 µl TE, pH 7.6 (if difficult, heat occasionally for 5 min at 65° C.), phenol extracted and precipitated with ethanol for 12 h at −20° C. (2.5 vols EtOH, 0.1 vol 3M NaAc, pH 5.2). The RNA was collected by centrifugation, washed in 70% EtOH, and resuspended in a minimum volume of DEPC-DIW. The RNA concentration was determined by measuring $OD_{260/280}$.

Isolation of poly(A) $^+$RNA: The poly(A) $^+$RNAs were isolated by oligo(dT)-cellulose affinity chromatography (Aviv & Leder, 1972). Typically, 0.2 g of oligo(dT) cellulose (Boehringer Mannheim) was preswollen in 10 ml of 1×column loading buffer (20 mM-Tris-Cl, pH 7.6, 0.5 M NaCl, 1 mM EDTA, 0.1% SDS), loaded onto a DEPC-treated, plugged plastic column (Poly Prep Chromatography Column, Bio Rad), and equilibrated with 20 ml 1×loading buffer. The total RNA was heated at 65° C. for 8 min., quenched on ice for 5 min, and after addition of 1 vol 2×column loading buffer to the RNA sample loaded onto the column. The eluate was collected and reloaded 2–3 times by heating the sample as above and quenching on ice prior to each loading. The oligo(dT) column was washed with 10 vols of 1×loading buffer, then with 3 vols of medium salt buffer (20 mM Tris-Cl, pH 7.6, 0.1 M NaCl, 1 mM EDTA, 0.1% SDS), followed by elution of the poly(A) $^+$RNA with 3 vols of elution buffer (10 mM Tris-Cl, pH 7.6, 1 mM EDTA, 0.05% SDS) preheated to +65° C., by collecting 500 µl fractions. The $OD_{260}$ was read for each collected fraction, and the mRNA containing fractions were pooled and ethanol precipitated at −20° C. for 12h. The poly(A) $^+$RNA was collected by centrifugation, resuspended in DEPC-DIW and stored in 5–10 µg aliquots at −80° C.

Northern blot analysis: The poly(A)$^+$RNAs (5 µg/sample) from various mycelia were electrophoresed in 1.2 agarose-2.2 M formaldehyde gels (Sambrook et al., 1989) and blotted to nylon membranes (Hybond-N, Amersham) with 10×SSC (Sambrook et al., 1989) as transfer buffer. Three random-primed (Feinberg & Vogelstein, 1983) $^{32}$P-labeled cDNA probes were used in individual hybridizations: 1) a 1.3 kb Not I-Spe I fragment for polygalacturonase I from *A. aculeatus* (described in PCT/DK93/00445), 2) a 1.3 kb Not I-Spe I fragment encoding endoglucanase I from *A. aculeatus* (described in DK 0419/92) and 3) a 1.2 kb Eag I fragment for galactanase I from *A. aculeatus* (described in WO 92/13945). Northern hybridizations were carried out in 5×SSC (Sambrook et al., 1989), 5×Denhardt's solution (Sambrook et al., 1989), 0.5% SDS (w/v) and 100 µg/ml denatured salmon sperm DNA with a probe concentration of ca. 2 ng/ml for 16 h at 65° C. followed by washes in 5×SSC at 65° C. (2×15 min), 2×SSC, 0.5% SDS (1×30 min), 0.2×SSC, 0.5% SDS (1×30 min), and 5×SSC (2×15 min). After autoradiography at −80° C. for 12 h, the probe #1 was removed from the filter according to the manufacturer's instructions and rehybridized with probe #2, and eventually with probe #3. The RNA ladder from Bethesda Research Laboratories was used as a size marker.

cDNA Synthesis:

First strand synthesis: Double-stranded cDNA was synthesized from 5 µg of *A. aculeatus* poly (A)$^°$ RNA by the RNase H method (Gubler & Hoffman 1983, Sambrook et al., 1989) using the hairpin modification. The poly(A)$^+$ RNA (5 µg in 5 µl of DEPC-treated water) was heated at 70° C. for 8 min., quenched on ice, and combined in a final volume of 50 µl with reverse transcriptase buffer (50 mM Tris-Cl, pH 8.3, 75 mM KCl, 3 mM MgCl2, 10 mM DTT, Bethesda Research Laboratories) containing 1 mM each dNTP (Pharmacia), 40 units of human placental ribonuclease inhibitor (RNasin, Promega), 10 µg of oligo(dT)$_{12–18}$ primer (Pharmacia) and 1000 units of SuperScript II RNase H-reverse transcriptase (Bethesda Research Laboratories). First-strand cDNA was synthesized by incubating the reaction mixture at 45° C. for 1 h.

Second strand synthesis: After synthesis 30 µl of 10 mM Tris-Cl, pH 7.5, 1 mM EDTA was added, and the mRNA:cDNA hybrids were ethanol precipitated for 12 h at −20° C. by addition of 40 µg glycogen carrier (Boehringer Mannheim) 0.2 vols 10 M $NH_4Ac$ and 2.5 vols 96% EtOH. The hybrids were recovered by centrifugation, washed in 70% EtOH, air dried and resuspended in 250 µl of second strand buffer (20 mM Tris-Cl, pH 7.4, 90 mM KCl, 4.6 mM MgCl2, 10 mM $(NH_4)_2SO_4$, 16 µM βNAD$^+$) containing 100 µM each dNTP, 44 units of *E. coli* DNA polymerase I (Amersham), 6.25 units of RNase H (Bethesda Research Laboratories) and 10.5 units of *E. coli* DNA ligase (New England Biolabs). Second strand cDNA synthesis was performed by incubating the reaction tube at 16° C. for 3 h, and the reaction was stopped by addition of EDTA to 20 mM final concentration followed by phenol extraction.

Mung bean nuclease treatment: The double-stranded (ds) cDNA was ethanol precipitated at −20° C. for 12 h by addition of 2 vols of 96% EtOH, 0.1 vol 3 M NaAc, pH 5.2, recovered by centrifugation, washed in 70% EtOH, dried (SpeedVac), and resuspended in 30 µl of Mung bean nuclease buffer (30 mM NaAc, pH 4.6, 300 mM NaCl, 1 mM ZnSO4, 0.35 mM DTT, 2% glycerol) containing 36 units of Mung bean nuclease (Bethesda Research Laboratories). The single-stranded hair-pin DNA was clipped by incubating the reaction at 30° C. for 30 min, followed by addition of 70 µl 10 mM Tris-Cl, pH 7.5, 1 mM EDTA, phenol extraction, and ethanol precipitation with 2 vols of 96% EtOH and 0.1 vol 3M NaAc, pH 5.2 at −20° C. for 12 h.

Blunt-ending with T4 DNA polymerase: The ds cDNA was blunt-ended with T4 DNA polymerase in 50 µl of T4 DNA polymerase buffer (20 mM Tris-acetate, pH 7.9, 10 mM MgAc, 50 mM KAc, 1 mM DTT) containing 0.5 mM each dNTP and 7.5 units of T4 DNA polymerase (Invitrogen) by incubating the reaction mixture at +37° C. for 15 min. The reaction was stopped by addition of EDTA to 20 mM final concentration, followed by phenol extraction and ethanol precipitation.

Adaptor ligation and size selection: After the fill-in reaction the cDNA was ligated to non-palindromic BstX I adaptors (1 µg/µl, Invitrogen) in 30 µl of ligation buffer (50 mM Tris-Cl, pH 7.8, 10 mM MgCl2, 10 mM DTT, 1 mM ATP, 25 µg/ml bovine serum albumin) containing 600 pmol BstX I adaptors and 5 units of T4 ligase (Invitrogen) by incubating the reaction mix at +16° C. for 12 h. The reaction was stopped by heating at +70° C. for 5 min, and the adapted cDNA was size-fractionated by agarose gel electrophoresis (0.8% HSB-agarose, FMC) to separate unligated adaptors and small cDNAs. The cDNA was size-selected with a cut-off at 0.7 kb, and the cDNA was electroeluted from the agarose gel in 10 mM Tris-Cl, pH 7.5, 1 mM EDTA for 1 h at 100 volts, phenol extracted and ethanol precipitated at −20° C. for 12 h as above.

Construction of cDNA libraries: The adapted, ds cDNA was recovered by centrifugation, washed in 70% EtOH and resuspended in 25 ml DIW. Prior to large-scale library ligation, four test ligations were carried out in 10 µl of ligation buffer (same as above) each containing 1 µl ds cDNA (reaction tubes #1–#3), 2 units of T4 ligase (Invitrogen) and 50 ng (tube #1), 100 ng (tube #2) and 200 ng (tubes #3 and #4) Bst XI cleaved yeast expression vector either pYES 2.0 vector Invitrogen or yHD13). The ligation reactions were performed by incubation at +16° C. for 12 h, heated at 70° C. for 5 min, and 1 µl of each ligation electroporated (200 Ω, 2.5 kV, 25 µF) to 40 µl competent E. coli 1061 cells (OD600=0.9 in 1 liter LB-broth, washed twice in cold DIW, once in 20 ml of 10% glycerol, resuspended in 2 ml 10% glycerol). After addition of 1 ml SOC to each transformation mix, the cells were grown at +37° C. for 1 h , 50 µl plated on LB+ampicillin plates (100 µg/ml) and grown at +37° C. for 12h.

Using the optimal conditions a large-scale ligation was set up in 40 µl of ligation buffer containing 9 units of T4 ligase, and the reaction was incubated at +16° C. for 12 h. The ligation reaction was stopped by heating at 70° C. for 5 min, ethanol precipitated at −20° C. for 12 h, recovered by centrifugation and resuspended in 10 µl DIW. One µl aliquots were transformed into electrocompetent E. coli 1061 cells using the same electroporation conditions as above, and the transformed cells were titered and the library plated on LB+ampicillin plates with 5000–7000 c.f.u./plate. To each plate was added 3 ml of medium. The bacteria were scraped off, 1 ml glycerol was added and stored at −80° C. as pools. The remaining 2 ml were used for DNA isolation. If the amount of DNA was insufficient to give the required number of yeast transformants, large scale DNA was prepared from 500 ml medium (TB) inoculated with 50 µl of −80° C. bacterial stock propagated overnight.

Construction of yeast libraries: To ensure that all the bacterial clones were tested in yeast, a number of yeast transformants 5 times larger than the number of bacterial clones in the original pools was set as the limit.

One µl aliquots of purified plasmid DNA (100 ng/µl) from individual pools were electroporated (200 Ω, 1.5 kV, 25 µF) into 40 µl competent S. cerevisiae JG 169 cells (OD600=1.5 in 500 ml YPD, washed twice in cold DIW, once in cold 1 M sorbitol, resuspended in 0.5 ml 1 M sorbitol, Becker & Guarante, 1991). After addition of 1 ml 1M cold sorbitol, 80 µl aliquots were plated on SC+glucose - uracil to give 250–400 c.f.u./plate and incubated at 30° C. for 3–5 days.

Construction of an Aspergillus expression vector: The vector pHD414 is a derivative of the plasmid p775 (described in EP 238 023). In contrast to this plasmid, pHD 414 has a string of unique restriction sites between the promoter and the terminator. The plasmid was constructed by removal of an approximately 200 bp long fragment (containing undesirable RE sites) at the 3' end of the terminator, and subsequent removal of an approximately 250 bp long fragment at the 5' end of the promoter, also containing undesirable sites. The 200 bp region was removed by cleavage with NarI (positioned in the pUC vector) and XbaI (just 3' to the terminator), subsequent filling in the generated ends with Klenow DNA polymerase +dNTP, purification of the vector fragment on gel and religation of the vector fragment. This plasmid was called pHD413. pHD413 was cut with StuI (positioned in the 5' of the promoter) and PvuII (in the pUC vector), fractionated on gel and religated. The plasmid pHD 414 is shown in FIG. 2.

Transformation of Aspergillus oryzae or Aspergillus niger (general procedure)

100 ml of YPD (Sherman et al., Methods in Yeast Genetics, Cold Spring Harbor Laboratory, 1981) is inoculated with spores of A. oryzae or A. niger and incubated with shaking at 37° C. for about 2 days. The mycelium is harvested by filtration through miracloth and washed with 200 ml of 0.6 M MgSO$_4$. The mycelium is suspended in 15 ml of 1.2 M MgSO$_4$. 10 mM NaH$_2$PO$_4$, pH=5.8. The suspension is cooled on ice and 1 ml of buffer containing 120 mg of Novozym® 234, batch 1687 is added. After 5 minutes 1 ml of 12 mg/ml BSA (Sigma type H25) is added and incubation with gentle agitation continued for 1.5–2.5 hours at 37° C. until a large number of protoplasts is visible in a sample inspected under the microscope.

The suspension is filtered through miracloth, the filtrate transferred to a sterile tube and overlayered with 5 ml of 0.6 M sorbitol, 100 mM Tris-HCl, pH=7.0. Centrifugation is performed for 15 minutes at 100 g and the protoplasts are collected from the top of the MgSO$_4$ cushion. 2 volumes of STC (1.2 M sorbitol, 10 mM Tris-HCl, pH=7.5. 10 mM CaCl$_2$) are added to the protoplast suspension and the mixture is centrifugated for 5 minutes at 1000 g. The protoplast pellet is resuspended in 3 ml of STC and repelleted. This is repeated. Finally the protoplasts are resuspended in 0.2–1 ml of STC.

100 µl of protoplast suspension is mixed with 5–25 µg of the appropriate DNA in 10 µl of STC. Protoplasts are mixed with p3SR2 (an A. nidulans amdS gene carrying plasmid). The mixture is left at room temperature for 25 minutes. 0.2 ml of 60% PEG 4000 (BDH 29576). 10 mM CaCl$_2$ and 10 mM Tris-HCl, pH=7.5 is added and carefully mixed (twice) and finally 0.85 ml of the same solution is added and carefully mixed. The mixture is left at room temperature for 25 minutes, spun at 2500 g for 15 minutes and the pellet is resuspended in 2 ml of 1.2 M sorbitol. After one more sedimentation the protoplasts are spread on the appropriate plates. Protoplasts are spread on minimal plates (Cove Biochem.Biophys.Acta 113 (1966) 51–56) containing 1.0 M sucrose, pH=7.0, 10 mM acetamide as nitrogen source and 20 mM CsCl to inhibit background growth. After incubation for 4–7 days at 37° C. spores are picked and spread for single colonies. This procedure is repeated and spores of a single colony after the second reisolation is stored as a defined transformant.

Media:

YPD: 10 g yeast extract, 20 g peptone, $H_2O$ to 810 ml. Autoclaved, 90 ml 20% glucose (sterile filtered) added.

10×Basal salt: 66.8 g yeast nitrogen base, 100 g succinic acid, 60 g NaOH, $H_2O$ ad 1000 ml, sterile filtered.

SC-URA: 90 ml 10×Basal salt, 22.5 ml 20% casamino acids, 9 ml 1% tryptophan, $H_2O$ ad 806 ml, autoclaved, 3.6 ml 5% threonine and 90 ml 20% glucose or 20% galactose added.

SC-H broth: 7.5 g/l yeast nitrogen base without amino acids, 11.3 g/l succinic acid, 6.8 g/l NaOH, 5.6 g/l casamino acids without vitamins, 0.1 g/l tryptophan. Autoclaved for 20 min. at 121° C. After autoclaving, 10 ml of a 30% galactose solution, 5 ml of a 30% glucose solution and 0.4 ml of a 5% threonine solution were added per 100 ml medium.

SC-H agar: 7.5 g/l yeast nitrogen base without amino acids, 11.3 g/l succinic acid, 6.8 g/l NaOH, 5.6 g/l casamino acids without vitamins, 0.1 g/l tryptophan, and 20 g/l agar (Bacto). Autoclaved for 20 min. at 121° C. After autoclaving, 55 ml of a 22% galactose solution and 1.8 ml of a 5% threonine solution were added per 450 ml agar.

YNB-1 agar: 3.3 g/l $KH_2PO_4$, 16.7 g/l agar, pH adjusted to 7. Autoclaved for 20 min. at 121° C. After autoclaving, 25 ml of a 13.6% yeast nitrogen base without amino acids, 25 ml of a 40% glucose solution, 1.5 ml of a 1% L-leucine solution and 1.5 ml of a 1% histidine solution were added per 450 ml agar.

YNB-1 broth: Composition as YNB-1 agar, but without the agar.

FG-4-Agar: 35 g/L agar, 30 g/L Soy bean meal, 15 g/L maltodextrin (Glucidex 6), 5 g/L Bacto pepton, pH 7. Autoclaved 40 min at 121° C.

FG-4 medium: 30 g/L Soy bean meal, 15 g/L maltodextrin (Glucidex 6), 5 g/L Bacto peptone. Autoclaved 40 min at 121° C.

MDU-2 medium: 45 g/L maltose, 1 g/L $MgSO_4$-7 $H_2O$, 1 g/L NaCl, 2g/L $K_2SO_4$, 12 g/L $KH_2PO_4$, 0.1 ml/L Pluronic 61 L, 0.5 ml/L Trace metal solution. pH 5.0. Autoclaved 20 min at 121° C. 15 ml/L 50% sterile filtered urea is added after autoclaving.

AZCL galactan from lupin: available from Megazyme, Australia.

AZCL arabinan from sugar beet: available from Megazyme, Australia.

Dyeing and Crosslinking of RG-Substrate

Hairy regions from apples (MHR) were extracted from apples according to the method of Schols et al. (1990b). In order to remove arabinan sidechains from this rhamnogalacturonan 25 g of MHR was dissolved in 500 ml of water and 1.9 ml concentrated TFA was added. After 1 hour at 100° C. the solution was dialysed against distilled water. The dialysed material was dyed by a modification of the method described by Call and Emeis, 1983 (J. Food-Biochem, 7(1): 43–52) by adding NaOH to pH 7.0, 5 g Cibacron C blau and 7.5 g Cibacron C gelb to the content of the dialysis bag and adding 25 g of $Na_2SO_4$ over a period of 10 minutes at 50° C. After 30 minutes 3.75 g of $Na_3PO_4$ was added and pH was adjusted to 11. pH was adjusted to 7 after 1 hour and 2.5 l of ethanol was added. The precipitate was recovered by centrifugation and was redissolved and reprecipitated three times. To crosslink the material 0.5 g of the dyed dehaired rhamnogalacturonan was dissolved in 50 ml of water, pH was adjusted to 12 and 2.5 ml Divinylsulphone and 200 ml ethanol was added. After 1 hour at room temperature the mixture was neutralised with HCl, centrifuged and the precipitate washed in boiling water 2 times. Purified A. aculeatus RGase II obtained as described in WO 92/19728 and pure arabinanase and galactanase from MegaZyme were used to test the specificity of the assay.

The purified A. aculeatus RGase II dissolved the crosslinked rhamnogalacturonan with a concomitant release of green colour. The arabinanase and galactanase did not dissolve the substrate.

Fed Batch Fermentation

The medium used for fed-batch fermentation of RGase I by A. oryzae comprised maltodextrin as a carbon source, urea as a nitrogen source and yeast extract.

The fed batch fermentation was performed by innoculating a shake flask culture of the A. oryzae host cells in question into a medium comprising 3.5% of the carbon source and 0.5% of the nitrogen source. After 24 hours of cultivation at pH 5.0 and 34° C. the continuous supply of additional carbon and nitrogen sources were initiated. The carbon source was kept as the limiting factor and it was secured that oxygen was present in excess. The fed batch cultivation was continued for 4 days, after which the enzymes could be recovered.

Characterization of Enzymes

For pH optimum and temperature optimum determination, RGase activity was assayed on AZCL-galactan (from MegaZyme). 0.4% suspensions of AZCL-galactan were mixed 1:1 with 0.1M buffer (preferably acetate buffer, but for pH optimum citrate/trisodiumphosphate buffer systems were used) and a suitable amount of enzyme was added. Incubations were carried out in Eppendorf® thermomixers at 30° C. (except for temperature optimum) for 15 minutes before the enzyme was inactivated at 95° C. for 20 minutes. Centrifugation was carried out and the release of blue colour into the supernatant was measured in microtiter plates at 620 nm. The relative activity is defined as the activity divided by the activity at optimal pH or optimal temperature.

Size Exclusion Chromatography (SEC)

MHR was saponified by leaving a 2% solution at pH 12 for 1h at 50° C. The saponified MHR (MHR-S) was recovered by precipitation in ethanol. A 1% solution of MHR-S in 0.1M acetate buffer of optimal pH was added 10 μl of enzyme solution and incubation was carried out in thermomixers at 30° C. for 1, 2, 4 and 24 hours before heat-inactivation of enzyme. 25 μl of enzyme treated material was injected into three SEC-columns connected in series (TSK PW G4000, G3500 & G2500 including a guard column) and was eluted by 0.8 ml/min 0.4M sodium acetate buffer pH 3.0 supplied by a Dionex HPLC system. Eluting saccharides were detected by a Shimadzu RI detektor and collection of data was commenced 15 minutes after injection. Data were processed by Dionex software. Dextrans from Serva were used as molecular weight standards.

High Pressure Anion Exchange Chromatography (HPAEC)

The MHR-S digests were also analysed by anion-exchange chromatography using a Dionex HPLC system (Dionex Corporation, Sunnyvale, Calif.) equipped with a CarboPac PA1 column. This system was used for detection of saccharides as prescribed by the Dionex Corporation (Dionex Technical note TN 20). Eluents were A: 0.1M NaOH and B: 1M Sodium acetate in 0.1M NaOH. 25 µl of sample was injected and saccharides were eluted at 1 ml/min with a gradient of 15% B to 50% B within 40 minutes. Data were processed by Dionex software.

Degradation of Soy Polysaccharides

Soy remanens was prepared by jetcooking of soy flour at 115° C. for 4 minutes, then hydrolysing the protein with Alcalase® (Novo Nordisk A/S), recovering of the residue and then repeating the Alcalase® treatment and recovery of residue. The so obtained residue of soy polysaccharides is essentially free from protein and was spraydried.

To 1 ml of a 1% suspension of soy polysaccharide in 0.1M acetate buffer pH 5.0 is added a suitable amount of enzyme and the mixture is incubated for 0, 1, 2, 4, and 24 hours before heat inactivation and analysis by Size Exclusion Chromatography.

The enzymes added were RGase I described herein, an rhamnogalacturonan acetyl esterase, and a combination of these enzymes. The rhamnogalacturonan acetyl esterase used was the *A. aculeatus* rhamnogalacturonan acetyl esterase described in WO 15 93/20190.

Example 1

Cloning of RGase I

A library from *A. aculeatus* consisting of approx. $1.5 \times 10^6$ individual clones in 150 pools was constructed.

DNA was isolated from 20 individual clones from the library and subjected to analysis for cDNA insertion. The insertion frequency was found to be >90% and the average insert size was approximately 1400 bp.

DNA from some of the pools was transformed into yeast, and 50–100 plates containing 200–500 yeast colonies were obtained from each pool. After 3–5 days of growth, the agar plates were replica plated onto several sets of agar plates. One set of plates containing 0.1% AZCL galactan, potato or lupin (Megazyme), one set containing 0.2% dyed and crosslinked MHR-substrate and one set containing 0.1% AZCL-arabinan were then incubated for 3–5 days at 30° C. for detection of activity. Positive arabinanase and galactanase colonies were identified as colonies surrounded by a blue halo.

Positive RGase colonies were identified where the grains of insoluble MHR-substrate were dissolved.

The screening of yeast colonies yielded four clones possessing RGase activity. Upon DNA sequencing of the inserts it became evident that all four clones represented the same enzyme (RG I). From the DNA sequence it also became evident that this sequence did not correspond to the amino acid sequence of the purified RGase II disclosed in Wo 92/19728).

It was very surprisingly observed that the four rhamnogalacturonase positive colonies also could be detected on AZCL-galactan and AZCL-arabinan. The arabinanase and galactanase colonies on the other hand did not give positive reaction on the crosslinked rhamnogalacturonan, which verifies the results obtained in the testing with pure arabinanase and galactanase. Thus, AZCL-galactan and AZCL-arabinan can be used as unspecific substrates for RGases (and are concomitantly shown not to be specific for arabinanases or galactanases either), whereas the dyed and crosslinked dehaired rhamnogalacturonan is highly specific for RGases.

Cells from enzyme-positive colonies were spread for single colony isolation on agar, and an enzyme-producing single colony was selected for each of the positive colonies identified.

Characterization of positive clones: The positive clones were obtained as single colonies, the cDNA inserts were amplified directly from the yeast colony using biotinylated polylinker primers, purified by magnetic beads (Dynabead M-280, Dynal) system and characterized individually by sequencing the 5'-end of each cDNA clone using the chain-termination method (Sanger et al., 1977) and the Sequenase system (United States Biochemical). The DNA sequence of the enzyme gene is shown in SEQ ID No. 1 and the amino acid sequence deduced therefrom in SEQ ID No. 2. The DNA and amino acid sequence is further shown in Table 1 hereinafter. A comparison of the DNA and amino acid sequence of SEQ ID No. 2 with that of RGase II did not reveal any homology. Furthermore, no homologous sequences could be detected by a search in the EMBL/GenBank databases performed on the basis of SEQ ID Nos. 1 and 2.

Isolation of a cDNA gene for expression in Aspergillus: In order to avoid PCR errors in the gene to be cloned, the cDNA was isolated from the yeast plasmid by standard procedures as described below.

One or more of the positive colonies were inoculated into 20 ml YNB-1 broth in a 50 ml glass test tube. The tube was shaken for 2 days at 30° C. The cells were harvested by centrifugation for 10 min. at 3000 rpm.

The cells were resuspended in 1 ml 0.9 M sorbitol, 0.1 M EDTA, pH 7.5. The pellet was transferred to an Eppendorf tube, and spun for 30 seconds at full speed. The cells were resuspended in 0.4 ml 0.9 M sorbitol, 0.1 M EDTA, 14 mM β-mercaptoethanol. 100 µl 2 mg/ml Zymolase was added, and the suspension was incubated at 37° C. for 30 minutes and spun for 30 seconds. The pellet (spheroplasts) was resuspended in 0.4 ml TE. 90 µl of (1.5 ml 0.5 M EDTA pH 8.0, 0.6 ml 2 M Tris-Cl pH 8.0, 0.6 ml 10% SDS) was added, and the suspension was incubated at 65° C. for 30 minutes. 80 µl 5 M KOAc was added, and the suspension was incubated on ice for at least 60 minutes and spun for 15 minutes at full speed. The supernatant was transferred to a fresh tube which was filled with EtOH (room temp.) followed by thorough but gentle mixing and spinning for 30 seconds. The pellet was washed with cold 70% ETOH, spun for 30 seconds and dried at room temperature. The pellet was resuspended in 50 µl TE and spun for 15 minutes. The supernatant was transferred to a fresh tube. 2.5 µl 10 mg/ml RNase was added, followed by incubation at 37° C. for 30 minutes and addition of 500 µl isopropanol with gentle mixing. The mixture was spun for 30 seconds, and the supernatant was removed. The pellet was rinsed with cold 96% EtOH and dried at room temperature. The DNA was dissolved in 50 µl water to a final concentration of approximately 100 µl/ml.

The DNA was transformed into *E. coli* by standard procedures. Two *E. coli* colonies were isolated from each of the transformations and analysed with the restriction enzymes HindIII and XbaI which excised the DNA insert. DNA from one of these clones was retransformed into yeast strain JG169.

The DNA sequences of several of the positive clones where partially determined. The DNA sequence encoding RGase I of the invention is shown in SEQ ID No. 1. The deduced amino acid sequence is shown in SEQ ID No. 2.

Example 2
Expression of Rhamnogalacturonase I (RGase I)

In order to express the genes in Aspergillus, cDNA was isolated from one or more representatives of each family by digestion with HindIII/XbaI or other appropriate restriction enzymes, size fractionation on a gel and purification and subsequently ligated to pHD414, resulting in the plasmid pGal-II. After amplification in *E. coli*, the plasmids were transformed into *A. oryzae* or *A. niger* according to the general procedure described above.

Test of *A. oryzae* Transformants

Each of the transformants was inoculated in the center of a Petri dish with FG-4 agar. After 5 days of incubation at 30° C. 4 mm diameter plugs were removed from the center of the colonies by a corkscrew. The plugs were embedded in a galactan overlayer gel, containing 0.1% AZCL galactan and 1% agarose in a buffer with an appropriate pH, and incubated overnight at 40° C. The RGase activity was identified as described above. Some of the transformants had halos which were significantly larger than the *Aspergillus oryzae* background. This demonstrates efficient expression of RGase in *Asperzgilus oryzae*. The 8 transformants with the highest RGase activity were selected and inoculated and maintained on YPG-agar.

Each of the 8 selected transformants were inoculated from YPG-agar slants on 500 ml shake flask with FG-4 and MDU-2 media. After 3–5 days of fermentation with sufficient agitation to ensure good aeration, the culture broths were centrifuged for 10 minutes at 2000 g and the supernatants were analyzed.

A volume of 15 µl of each supernatant was applied to 4 mm diameter holes punched out in a 0.1% AZCL galactan overlayer gel (25 ml in a 13 cm diameter Petri dish). The RGase activity was identified by the formation of a blue halo on incubation.

Fed Batch Fermentation

Subsequently, RGase I was produced by fed batch fermentation of *A. oryzae* expressing the enzyme using the procedure described above.

Example 3
Purification of RGase I

The culture supernatant from fermentation of *Aspergillus oryzae* or *A. niger* expressing the recombinant enzyme is centrifuged at 5000×g and filtered through a 0.2 µm filter to remove the mycelia. 35–50 ml of the filtered supernatant containing 30–70 mg of the recombinant enzyme is ultrafiltrated in an Amicon 200 ml ultrafiltration device with a 10 kDa membrane to achieve 10 fold concentration. This concentrate is diluted 100 times in 20 mM Tris pH 8.0 in two successive rounds of ultrafiltration in the same device, and the final volume is adjusted to approximately 40 ml. This ultrafiltrated sample is loaded at 2 ml/min on a Pharmacia HR16/10 Fast Flow Q Sepharose anion exchanger equilibrated in 20 mM Tris pH 8.0. After the sample has been applied, the column is washed with two column volumes 20 mM Tris pH 8.0, and bound proteins are eluted with a linear increasing NaCl gradient from 0 to 0.5 M NaCl in 20 mM Tris pH 8.0. RGase I elutes at approximately 0.3 M NaCl, and fractions containing RGase I activity are pooled and concentrated by ultrafiltration. RGase I in this fraction was purified to more than 99% homogeneity.

Example 4
Characterization of RGase I and II

After transformation, expression and purification as described above, RGase I was characterized. For comparison, some characterizing data for *A. aculeatus* RGase II (obtained as described in WO 92/19728) are included.

AZCL-galactan can be used for detection of RGase activity since it was discovered that this substrate is not a pure galactan but is composed of fragments of rhamnoglacturonan backbone with galactan sidechains attached to it. The MW and pI for RG I can be seen in the table below and the pH optimum and temperature optimum from FIG. 3 and FIG. 4, respectively.

|  | RG I |
| --- | --- |
| Mw | 59.2 |
| pI | 5.1 |
| pH optimum | 6.0 |
| pH stability | >6.0 |
| temp. optimum | 50° C. |
| temp. stability | <60° C. |

It is seen that RG I is most active about pH 6.0 whereas RG II is most active around pH 3.5. This signifies the different application possibilities of the two enzymes, RGase I being much more active in the neutral pH range.

Both enzymes were found to be more active in acetate buffer than in phosphate or citrate buffer and therefore all experiments except the pH optimum were carried out in acetate buffer of the optimal pH for the enzyme. Both enzymes became partly inactivated after 1 hour at 60° C.

The molecular weight of RGase I (59.2 kD) is lower than the molecular weight of RGase II (62 kD), and polyclonal antibodies raised against RGase II do not cross-react with RGase I. The glycosylation differs significantly between the two RGases. RGase II (but not RGase I) reacts with GNA lectin which is specific for terminal β-1,3, β-1,2 or β-1,6 bound mannose in protein attached glycan structures.

The SEC degradation patterns obtained on MHR-S with RG I and RG II can be seen from FIGS. 5 and 6. The smallest oligosaccharide obtained can be estimated to have a DP of approximately DP 6–10. From studies on the purified RG II from *A. aculeatus* it is known that RG II hydrolyses between galacturonic acid and rhamnose leaving rhamnose as the non-reducing residue (Colquhoun et al. (1990)). The SEC analysis shows that the degradation products of the two RGases are of the same molecular weight after 24 hours (see FIGS. 5 and 6). The two enzymes are dosed in order to give the same activity on AZCL-galactan. However, it can be seen that on MHR-S RG II is more active than RGI, which shows that the two enzymes have very different substrate specificity. When the degradation products are analysed by anion exchange chromatography different chromatograms are obtained with the two enzymes. The RG I oligomer peaks elute much later than the RG II oligomers (see FIGS. 7 and 8). This is not due to the RG I oligomers being larger, since the SEC analysis showed that the oligomers have the same size. It is known that oligomers with a deoxyhexose (rhamnose or fucose which elute very early from the PA1 column) at the non-reducing end tend to elute much earlier than even smaller oligomers with no deoxyhexose attached (McDougall & Fry (1991)). Thus the results obtained with the RGI degradation products shows that RGI hydrolyses at the other side of the rhamnose leaving galacturonic acid as the non-reducing end. This mode of action of a RGase has never been reported before and therefore the activity possessed by RG I must be considered to be a completely new type of enzyme activity.

Example 5
Extraction of Soluble Fibres from Soy

From the SEC of the enzyme treated soy polysaccharides (obtained as described in the Materials and Methods section-above) the peak area can be obtained, cf FIG. 9 which shows the degradation obtained by RGase I. When compared to the area obtained with a 1% dextran solution it can be calculated that RG I can solubilize about 25% of the soy polysaccharides and the combination of RG I and the *A. aculeatus* rhamnogalacturonan acetyl esterase (RGAE) (obtained as described in Wo 93/20190) about 50%. This solubilized material has a surprisingly high molecular weight exceeding DP 500 (calculated from the dextfan standards). The high molecular weight of the solubilized polysaccharides and monosaccharide analysis show that the liberated material is pieces of rhamnogalacturonan with sidechains attached. Monosaccharide analysis has shown that these sidechains are predominately galactans and secondarily arabinans. Thus, the RG I can be used for extraction of hairy regions from soy which maintain a surprisingly high molecular weight. RGase II was found to be inferior to RGase I for these purposes. Similar results have been obtained with rape seed polysaccharides.

Example 6

Viscosity Reduction of Soy Flour by RGase 1

Soy flour treated with 1 AU/kg DS Alcalase® (Novo Nordisk A/S) for 2 hours at pH 6.4, 50° C. and 23% DS was jet cooked for 4 min. at 115° C. and pH 5.0. The resulting slurry was spray dried. 2×60 g of spray dried jet cooked soy were suspended in 180 and 190 g of deionized water, respectively. The slurries were homogenized in a Warring Blender (the power switch in position 4) for 2 min. and then transferred to 2×250ml beakers. pH was adjusted to 5.0 and the samples were heated to 50° C. on a water bath. When the temperature reached 50° C. in the samples, 10 ml of an enzyme solution of RGase 1 containing 170 mg emzyme was added to the low volume sample. The slurry was mixed well with a glas rod. The viscosity in the samples were measured after 24 hours of incubation on a Brookfield viscometer, model RVDVII, with spindle 91 (T-A), at 50 rpm. The viscosity in the enzyme sample was only 48% of that in the sample without enzyme, due to the action of RGase I. Thus, it has been shown that a substantial viscosity reduction may be obtained by use of only one carbohydrate degrading enzyme.

Example 7

Purification of Saponified Beet Pectic Hairy Regions

Sugar beet fibres were produced from whole beets. The beets where washed, mashed, and pressed at 60–70° C., water was added to the filter cake, before it was repressed. The press-cake was dried and designated beet fibres.

150 g beet fibre were incubated in 3 L 0.05 M sodium succinate pH 5 with 2 w/w % Pectinex Ultra SP (obtainable from Novo Nordisk A/S) for 24 hours at 40° C., the incubation was stopped by heating at 100° C. for 30 min, and centrifugated for 60 minutes at 10.000 g. The pellet was washed 3 times with distilled water and the supernatants were pooled and concentrated with Ultrafiltration (Nephross Andante HF, Organon Technika, cut off 5.000). The solution was dialysed 24 hours against distilled water at room temperature. The retentate was freeze dried. The retentate was designated beet pectic modified hairy regions.

The sugar composition of the beet pectic modified hairy regions was determined to be 4% rhamnose, 48% arabinose, 1% xylose, 11% galactose, 1% glucose and 34% anhydrous uronic acid. The neutral sugars were determined by G.L.C. after pretreatment (1 h, 30° C.) with aqueous 72% $H_2SO_4$ followed by hydrolysis with 1 M $H_2SO_4$ (3 h, 100° C.) and conversion of the products into alditol acetates (Englyst & Cummings, Analyst 109 (1984) 937–942). The aditol acetates were analysed on a glass column (3 m×2 mm i.d.), packed with Chrom WAW 80–100 mesh coated with 3% OV275 in a Carlo Erba Fractovap 2300 GC. The uronic acid were determined by the calorimetric assay described by A. E. R. Ahmed et al., 1977, Food Biochemistry 1: 361–365.

The beet pectic hairy regions was saponified as described by Schols et al. (1990a).

RGase I, corresponding to 473 μg pure enzyme protein pr/ml, obtained as described in Examples 2 and 3, and an equivalent activity of RGase II (corresponding to 44 μg/ml pure enzyme protein pr ml) obtained as described in WO 92/19728 were added to 4 mg/ml saponified beet pectic modified hairy regions obtained as described above in separate experiments. The degradation patterns were analyzed by HPSEC after 24 hours incubation at 40° C. in 50 mM sodium acetate pH 5.0 (preserved by $NaN_3$).

The HPSEC was performed as described in H. A. Schols et al. 1990 (Carbohydrat. Res. 206: 105–115) on a SP800 HPLC (Spectra Physics) equipped with three BioGel TSK colmns (each 300×7.5 mm) in series (40XL, 30XL, and 20XL, Bio-Rad Labs) in combination with a TSK XL guard column (40×6 mm) and eluted at 30° C. with 0.4 M acetic acid/sodium acetate (pH 3.0) at 0.8 ml/min. The eluate was monitored using a Shodex SE-61 Refractive Index detector.

The RGase II had only insignificant activity on the saponified beet pectic hairy regions, where the RGase I gave a significant degradation of the saponified beet pectic hairy regions as showed on the HPSEC chromatogramme, cf FIG. 10.

REFERENCES

P. Albersheim et al., Pure & Appl. Chem., Vol. 53, pp. 79–88, 1981.

Aviv, H. & Leder, P. 1972. Proc. Natl. Acad. Sci. U. S. A. 69: 1408–1412.

Axelsen N. et al., Blackwell Scientific Publications, 1973, Chapter 23

Becker, D. M. & Guarante, L. 1991. Methods Enzymol. 194: 182–187.

N. C. Carpita and D. M. Gebeaut, The Plant Journal, Vol. 3, No. 1, pp. 1–30, 1993.

Circle et al., 1978, in Smith, A. K. Editor: Soybeans: Chemistry and Technology, Vol 1, Proteins.

Chirgwin, J. M., Przybyla, A. E., MacDonald, R. J. & Rutter, W. J. 1979. Biochemistry 18: 5294–5299.

Colquhoun et al., 1990, Carbohydrate Research 206, pp. 131–144.

S. C. Fry, in The growing plant cell wall: chemical and metabolic analysis, Longman Scientific & Technical, 1988.

Gubler, U. & Hoffman, B. J. 1983. Gene 25: 263–269.

Johnstone A. and Thorpe R., Blackwell Scientific Publications, 1982 (more specifically pp. 27–31).

McDougall & Fry, 1991, Carbohyarate Research 219, pp. 123–132.

M. O'Neill et al., Methods in Plant Biochemistry, Vol. 2, pp. 415, 1990.

O. Ouchterlony, *Handbook of Experimental Immunology* (D. M. Weir, Ed.), Blackwell Scientific Publications, 1967, pp. 655–706)

T. Sakamoto et al., Biosci. Biotech. & Biochem., Vol. 57, No. 11, pp. 1837–1837, 1993.

Sambrook, J., Fritsch, E. F. & Maniatis, T. 1989. Molecular Cloning: A Laboratory Manual. Cold Spring Harbor Lab., Cold Spring Harbor, N.Y.

Sanger, F., Nicklen, S. & Coulson, A. R. 1977. Proc. Natl. Acad. Sci. U. S. A. 74: 5463–5467.

Schols et al., Carbohydrate Research 206 (1990a) 105–115.

Schols et al., Carbohydrate Research 206 (1990b) 117–129.

Searle-van Leeuwen et al., "Rhamnogalacturonan acetyl esterase: a novel enzyme from *Aspergillus aculeatus*, specific for the deacetylation of hairy (ramified) regions of pectin", Appl. Microbiol. Biotechnol., 38: p. 347–349, 1992

A. G. J. Voragen et al., Proceedings of the International Symposium on Plant Polymeric Carbohydrates, Berlin, Jul. 1–3, 1992, (F. Meuser, ed.), Royal Society of Chemistry, Cambridge, U.K.

TABLE 1

SEQUENCE LISTING
Nucleotide sequence of the rhg1 gene,
and the deduced primary structure of RGase
I from *A. aculeatus*. The proposed
signal sequence is
underlined, and the $NH_2$-terminal amino
acid sequence of the purified
rhamnogalacturonase from *A. japonicus*
is shown aligned with the homologous
region in the *A. aculeatus* enzyme.

```
                                                                     60
         *         *         *         *         *         *
CGGACAATGCTCAAAGCGTCGCTTCTGTCGTTCGTGGCCTTCACGGCCCAGGTCGCCCAC
         M   L   K   A   S   L   L   S   F   V   A   F   T   A   Q   V   A   H
                                                                    120
         *         *         *         *         *         *
GCGGCCTTTGGCATCACCACCAGCTCCAGCGCCTATGTCATCGACACCAACGCGCCAAAC
 A   A   F   G   I   T   T   S   S   S   A   Y   V   I   D   T   N   A   P   N
     A   F   G   I   T   T   S   S   S   A   Y   V   I   D   T   D   A   P   N
                                                                    180
         *         *         *         *         *         *
CAGCTGAAGTTCACCGTCAGCCGCAGCAGCTGCGACATTACCTCCATCATCCACTATGGC
 Q   L   K   F   T   V   S   R   S   S   C   D   I   T   S   I   I   H   Y   G
 Q   L   K   ?   T   V   S   R
                                                                    240
         *         *         *         *         *         *
ACGGAGCTGCAGTACTCCAGCCAGGGCAGTCACATTGGGTCGGGTCTGGGCTCTGCGACG
 T   E   L   Q   Y   S   S   Q   G   S   H   I   G   S   G   L   G   S   A   T
                                                                    300
         *         *         *         *         *         *
GTGACCGCCACGCAGTCCGGGGACTATATCAAGGTGACCTGTGTGACGGACACCTTGACG
 V   T   A   T   Q   S   G   D   Y   I   K   V   T   C   V   T   D   T   L   T
                                                                    360
         *         *         *         *         *         *
CAGTACATGGTGGTGCATAATGGGACCCAATCATTCACATGGCGACATATATCACTGCC
 Q   Y   M   V   V   H   N   G   D   P   I   I   H   M   A   T   Y   I   T   A
                                                                    420
         *         *         *         *         *         *
GAGCCGTCAATCGGCGAGCTGCGGTTCATCGCTCGACTGAATTCGGACCTGCTACCGACG
 E   P   S   I   G   E   L   R   F   I   A   R   L   N   S   D   L   L   P   T
                                                                    480
         *         *         *         *         *         *
AGGAGCCGTTTGGCGACGTTTCCACCACCGCTGACGGGACTGCCATTGAGGGATCAGATG
 R   S   R   L   A   T   F   P   P   P   L   T   G   L   P   L   R   D   Q   M
                                                                    540
         *         *         *         *         *         *
TGTTTTTGGTCGGCAGTGAAACCCGCAGCAAGTTCTACTAGAGCGAGCGATTTATCGACG
 C   F   W   S   A   V   K   P   A   A   S   S   T   R   A   S   D   L   S   T
                                                                    600
         *         *         *         *         *         *
ATCAGCGACACTGCATTGCCGGGGATGCCCACCGCCGTTTGCATGATCTTGAATCAATAC
 I   S   D   T   A   L   P   G   M   P   T   A   V   C   M   I   L   N   Q   Y
                                                                    660
         *         *         *         *         *         *
GAAAGCTCCTCCGGAGGTCCTTTCCACCGGGATATCAACTCGAACAACGGAGGGAGCTAC
 E   S   S   S   G   G   P   F   H   R   D   I   N   S   N   N   G   G   S   Y
                                                                    720
         *         *         *         *         *         *
AACGCCCTCTACTGGTACATGAACTCCGGCCACGTTCAAACCGAGTCCTACCGGATGGGT
 N   A   L   Y   W   Y   M   N   S   G   H   V   Q   T   E   S   Y   R   M   G
                                                                    780
         *         *         *         *         *         *
CTCCACGGCCCATACTCGATGTACTTTAGTCGCAGCGGTACCCCCAGCACCAGCATCGAT
 L   H   G   P   Y   S   M   Y   F   S   R   S   G   T   P   S   T   S   I   D
                                                                    840
         *         *         *         *         *         *
ACCTCATTCTTCGCCGACCTTGACATCAAAGGCTATGTTGCCGCCTCAGGCCGAGGCAAA
 T   S   F   F   A   D   L   D   I   K   G   Y   V   A   A   S   G   R   G   K
```

TABLE 1-continued

SEQUENCE LISTING
Nucleotide sequence of the rhg1 gene,
and the deduced primary structure of RGase
I from *A. aculeatus*. The proposed
signal sequence is
underlined, and the NH$_2$-terminal amino
acid sequence of the purified
rhamnogalacturonase from *A. japonicus*
is shown aligned with the homologous
region in the *A. aculeatus* enzyme.

```
                                                           900
       *         *         *         *         *         *
GTGGCCGGCACGGCATCCGGAGCAGACTCGAGCATGGATTGGGTGGTTCACTGGTACAAC
 V  A  G  T  A  S  G  A  D  S  S  M  D  W  V  V  H  W  Y  N
                                                           960
       *         *         *         *         *         *
GATGCGGCACAGTACTGGACTTATACCAGCTCCAGCGGCAGCTTCACCTCGCCCGCCATG
 D  A  A  Q  Y  W  T  Y  T  S  S  S  G  S  F  T  S  P  A  M
                                                          1020
       *         *         *         *         *         *
AAGCCCGGAACGTACACCATGGTCTATTACCAAGGCGAGTACGCGGTCGCCACGAGCTCG
 K  P  G  T  Y  T  M  V  Y  Y  Q  G  E  Y  A  V  A  T  S  S
                                                          1080
       *         *         *         *         *         *
GTCACCGTGTCCGCCGGATCAACCACAACGAAGAACATTTCGGGGTCCGTGAAGACCGGC
 V  T  V  S  A  G  S  T  T  T  K  N  I  S  G  S  V  K  T  G
                                                          1140
       *         *         *         *         *         *
ACTACCATTTTCAAGATTGGTGAATGGGACGGACAACCGACCGCGTTCCGCAACGCAGCC
 T  T  I  F  K  I  G  E  W  D  G  Q  P  T  A  F  R  N  A  A
                                                          1200
       *         *         *         *         *         *
AACCACGTCCGCATGCACCCCTCCGACTCGCGCATGCCCTCCTGGGGTCCACTGACCTAT
 N  H  V  R  M  H  P  S  D  S  R  M  P  S  W  G  P  L  T  Y
                                                          1260
       *         *         *         *         *         *
ACGGTTGGCAGTTCCGCTCTGACTGACTTCCCAATGGCCGTGTTCAAAAGCGTCAACAAC
 T  V  G  S  S  A  L  T  D  F  P  M  A  V  F  K  S  V  N  N
                                                          1320
       *         *         *         *         *         *
CCGGTCACCATCAAATTCACCGCCACATCCGCGCAGACCGGCGCAGCGACCCTGCGAATC
 P  V  T  I  K  F  T  A  T  S  A  Q  T  G  A  A  T  L  R  I
                                                          1380
       *         *         *         *         *         *
GGGACGACCTTGTCGTTTGCCGGTGGACGACCCCAGGCGACGATCAACAGCTACACAGGA
 G  T  T  L  S  F  A  G  G  R  P  Q  A  T  I  N  S  Y  T  G
                                                          1440
       *         *         *         *         *         *
AGCGCACCAGCCGCGCCGACAAACCTGGACTCTCGGGGCGTGACCCGCGGTGCGTACCGG
 S  A  P  A  A  P  T  N  L  D  S  R  G  V  T  R  G  A  Y  R
                                                          1500
       *         *         *         *         *         *
GGATTGGGCGAGGTGTATGATGTGTCCATCCCGTCGGGGACGATCGTCGCGGGAACAAAT
 G  L  G  E  V  Y  D  V  S  I  P  S  G  T  I  V  A  G  T  N
                                                          1560
       *         *         *         *         *         *
ACAATTACGATCAACGTGATCTCTGGCAGTTCGGGGGATACGTATTTGAGTCCGAACTTT
 T  I  T  I  N  V  I  S  G  S  S  G  D  T  Y  L  S  P  N  F
                                                          1620
       *         *         *         *         *         *
ATCTTTGATTGTGTGGAGTTGTTCCAGTAGCTGATTGTTTCTCGGGCTGTATGGTGCAGC
 I  F  D  C  V  E  L  F  Q  *
                                                          1680
       *         *         *         *         *         *
CGGGAGTAGATAGCTGTACTGGACAGTTCTAGTCGTATGTGGAGGAAAGACCTAAGATCA
                                                          1740
       *         *         *         *         *         *
ACTGAATTCATGACCTACTGTCATTTTCTGTTGAAGTATTGTTCTGCTTGAATAAAGGTA
       *         *         *
TGTGGTTCAGCCTGGCAAAAAAAAAAAAAAAAAAAAA
                   SEQ ID No. 1

CGGACAATGCTCAAAGCGTCGCTTCTGTCGTTCGTGGCCTTCACGGCCCAGGTCGCCCAC
GCGGCCTTTGGCATCACCACCAGCTCCAGCGCCTATGTCATCGACACCAACGCGCCAAAC
CAGCTGAAGTTCACCGTCAGCCGCAGCAGCTGCGACATTACCTCCATCATCCACTATGGC
ACGGAGCTGCAGTACTCCAGCCAGGGCAGTCACATTGGGTCGGGTCTGGGCTCTGCGACG
GTGACCGCCACGCAGTCCGGGGACTATATCAAGGTGACCTGTGTGACGGACACCTTGACG
CAGTACATGGTGGTGCATAATGGGGACCCAATCATTCACATGGCGACATATATCACTGCC
```

TABLE 1-continued

SEQUENCE LISTING
Nucleotide sequence of the rhg1 gene,
and the deduced primary structure of RGase
I from A. aculeatus. The proposed
signal sequence is
underlined, and the NH$_2$-terminal amino
acid sequence of the purified
rhamnogalacturonase from A. japonicus
is shown aligned with the homologous
region in the A. aculeatus enzyme.

```
GAGCCGTCAATCGGCGAGCTGCGGTTCATCGCTCGACTGAATTCGGACCTGCTACCGACG
AGGAGCCGTTTGGCGACGTTTCCACCACCGCTGACGGGACTGCCATTGAGGGATCAGATG
TGTTTTTGGTCGGCAGTGAAACCCGCAGCAAGTTCTACTAGAGCGAGCGATTTATCGACG
ATCAGCGACACTGCATTGCCGGGATGCCCACCGCCGTTTGCATGATCTTGAATCAATAC
GAAAGCTCCTCCGGAGGTCCTTTCCACCGGGATATCAACTCGAACAACGGAGGGAGCTAC
AACGCCCTCTACTGGTACATGAACTCCGGCCACGTTCAAACCGAGTCCTACCGGATGGGT
CTCCACGGCCCATACTCGATGTACTTTAGTCGCAGCGGTACCCCCAGCACCAGCATCGAT
ACCTCATTCTTCGCCGACCTTGACATCAAAGGCTATGTTGCCGCCTCAGGCCGAGGCAAA
GTGGCCGGCACGGCATCCGGAGCAGACTCGAGCATGGATTGGGTGGTTCACTGGTACAAC
GATGCGGCACAGTACTGGACTTATACCAGCTCCAGCGGCAGCTTCACCTCGCCCGCCATG
AAGCCCGGAACGTACACCATGGTCTATTACCAAGGCGAGTACGCGGTCGCCACGAGCTCG
GTCACCGTGTCCGCCGGATCAACCACAACGAAGAACATTTCGGGGTCCGTGAAGACCGGC
ACTACCATTTTCAAGATTGGTGAATGGGACGGACAACCGACCGCGTTCCGCAACGCAGCC
AACCACGTCCGCATGCACCCCTCCGACTCGCGCATGCCCTCCTGGGGTCCACTGACCTAT
ACGGTTGGCAGTTCCGCTCTGACTGACTTCCCAATGGCCGTGTTCAAAAGCGTCAACAAC
CCGGTCACCATCAAATTCACCGCCACATCCGCGCAGACCGGCGCAGCGACCCTGCGAATC
GGGACGACCTTGTCGTTTGCCGGTGGACGACCCCAGGCGACGATCAACAGCTACACAGGA
AGCGCACCAGCCGCGCCGACAAACCTGGACTCTCGGGGCGTGACCCGCGGTGCGTACCGG
GGATTGGGCGAGGTGTATGATGTGTCCATCCCGTCGGGGACGATCGTCGCGGGAACAAAT
ACAATTACGATCAACGTGATCTCTGGCAGTTCGGGGGATACGTATTTGAGTCCGAACTTT
ATCTTTGATTGTGTGGAGTTGTTCCAGTAGCTGATTGTTTCTCGGGCTGTATGGTGCAGC
CGGGAGTAGATAGCTGTACTGGACAGTTCTAGTCGTATGTGGAGGAAAGACCTAAGATCA
ACTGAATTCATGACCTACTGTCATTTTCTGTTGAAGTATTGTTCTGCTTGAATAAAGGTA
TGTGGTTCAGCCTGGCAAAAAAAAAAAAAAAAAAA
```

SEQ ID No. 2

```
M L K A S L L S F V A F T A Q V A H
A A F G I T T S S S A Y V I D T N A P N
Q L K F T V S R S S C D I T S K I I H Y G
T E L Q Y S S Q G S H I G S G L G S A T
V T A T Q S G D Y I K V T C V T D T L T
Q Y M V V H N G D P I I H M A T Y I T A
E P S I G E L R F I A R L N S D L L P T
R S R L A T F P P P L T G L P L R D Q M
C F W S A V K P A A S S T R A S D L S T
I S D T A L P G M P T A V C M I L N Q Y
E S S S G G P F H R D I N S N N G G S Y
N A L Y W Y M N S G H V Q T E S Y R M G
L H G P Y S M Y F S R S G T P S T S I D
T S F A D L D I K G Y V A A S G R G K
V A G T A S G A D S S M D W V V H W Y N
D A A Q Y W T Y T S S S G S F T S P A M
K P G T Y T M V Y Y Q G E Y A V A T S S
V T V S A G S T T T K N I S G S V K T G
T T I F K I G E W D G Q P T A F R N A A
N H V R M H P S D S R M P S W G P L T Y
T V G S S A L T D F P M A V F K S V N N
P V T I K F T A T S A Q T G A A T L R I
G T T L S F A G G R P Q A T I N S Y T G
S A P A A P T N L D S R G V T R G A Y R
G L G E V Y D V S I P S G T I V A G T N
T I T I N V I S G S S G D T Y L S P N F
I F D C V E L F Q
```

We claim:

1. An animal feed composition comprising one or more of soy, pea or rapeseed, or other material derived from Fabales or Cruciferaceae, and an enzyme having rhamnogalacturonase activity, wherein the enzyme having rhamnogalacturonase activity cleaves a rhamnogalacturonan backbone to produce rhamnose as a non-reducing end (RGase II).

2. An animal feed composition comprising one or more of soy, pea or rapeseed, or other material derived from Fabales or Cruciferaceae, and an enzyme having rhamnogalacturonase activity, wherein the enzyme having rhamnogalacturonase activity (RGase I):

(a) cleaves a rharnnogalacturonan backbone to produce galacturonic acid as a non-reducing end;

(b) depolymerizes hairy regions from a soy bean material; and (c) depolymerizes saponified hairy regions from a sugar beet material.

3. An animal feed composition comprising one or more of soy, pea, or rapeseed, or other material derived from Fabales or Cruciferaceae, and an enzyme having rhamnogalacturonase activity, wherein the enzyme is one of:
- (a) a protein encoded by nucleotides 64–1587 of the DNA sequence of SEQ ID NO: 1;
- (b) a protein encoded by a DNA sequence which hybridizes to the same probe as nucleotides 64–1587 of SEQ ID NO: 1 under conditions of presoaking in 5×SSC and prehybridizing for 1 hour at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labeled probe for 18 h at ~40° C., followed by washing three times in 2×SSC, 0.2% SDS at 40° C. for 30 minutes; or
- (c) an amino acid sequence comprising amino acids 20–527 of the sequence of SEQ ID NO:2.

4. The animal feed of claim 1, further comprising an enzyme having rhamnogalacturonan acetyl esterase activity.

5. A method of producing an animal feed, comprising adding an enzyme having rhamnogalacturonase activity to one or more of soy, pea or rapeseed, or other material derived from Fabales or Cruciferaceae, wherein the enzyme having rhamnogalacturonase activity cleaves a rhamnogalacturonan backbone to produce rhamnose as a non-reducing end (RGase II).

6. A method for increasing the digestibility of an animal feed comprising adding an enzyme having rhamnogalacturonase activity to one or more of soy, pea or rapeseed, or other material derived from Fabales or Cruciferaceae, wherein the enzyme having rhamnogalacturonase activity cleaves a rhamnogalacturonan backbone to produce rhamnose as a non-reducing end (RGase II).

7. A method for reducing the viscosity of a feed comprising adding to the feed an enzyme having rhamnogalacturonase activity to one or more of soy, pea or rapeseed, or other material derived from Fabales or Cruciferaceae, wherein the enzyme having rhamnogalacturonase activity cleaves a rhamnogalacturonan backbone to produce rhamnose as a non-reducing end (RGase II).

8. The animal feed of claim 2, further comnprising an enzyme having rhamnogalacturonan acetyl esterase activity.

9. A method for increasing the digestibility of an animal feed comprising adding an enzyme having rhamnogalacturonase activity to one or more of soy, pea or rapeseed, or other material derived from Fabales or Cruciferaceae, wherein the enzyme having rhamnogalacturonase activity (RGase I):
- (a) cleaves a rhamnogalacturonan backbone to produce galacturonic acid as a non-reducing end;
- (b) depolymerizes hairy regions from a soy bean material; and
- (c) depolymerizes saponified hairy regions from a sugar beet material.

10. A method for reducing the viscosity of a feed comprising adding to the feed an enzyme having rhamnogalacturonase activity to one or more of soy, pea or rapeseed, or other material derived from Fabales or Cruciferaceae, wherein the enzyme having rhamnogalacturonase activity (RGase I):
- (a) cleaves a rhamnogalacturonan backbone to produce galacturonic acid as a non-reducing end;
- (b) depolymerizes hairy regions from a soy bean material, and
- (c) depolymerizes saponified hairy regions from a sugar beet material.

11. The animal feed of claim 3, further comprising an enzyme having rhamnogalacturonan acetyl esterase activity.

12. An animal feed composition comprising one or more of soy, pea or rapeseed, or other material derived from Fabales or Cruciferaceae, and an enzyme having rhamnogalacturonase activity, wherein the enzyme is one of:
- (a) a protein encoded by nucleotides 64–1587 of the DNA sequence of SEQ ID NO: 1,
- (b) a protein encoded by a DNA sequence which hybridizes to the same probe as nucleotides 64–1587 of SEQ ID NO: 1 under conditions of presoaking in 5×SSC and prehybridizing for 1 hour at ~40° C. in a solution of 5×SSC, 5×Denhardt's solution, 50 mM sodium phosphate, pH6.8, and 50 µg of denatured sonicated calf thymus DNA, followed by hybridization in the same solution supplemented with 50 µCi 32-P-dCTP labeled probe for 18 h at ~40° C., followed by washing three times in 2×SSC, 0.2% SDS at 40° C. for 30 minutes; or
- (c) an amino acid sequence comprising amino acids 20–527 of the sequence of SEQ ID NO:2.

13. A method for increasing the digestibility of an animal feed comprising adding an enzyme having rhamnogalacturonase activity to one or more of soy, pea or rapeseed, or other material derived from Fabales or Cruciferaceae, wherein the enzyme is one of:
- (a) a protein encoded by nucleotides 64–1587 of the DNA sequence of SEQ ID NO: 1;
- (b) a protein encoded by a DNA sequence which hybridizes to the same probe as nucleotides 64–1587 of SEQ ID NO: 1 under conditions of presoaking in 5×SSC and prehybridizing for 1 hour at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labeled probe for 18 h at ~40° C., followed by washing three times in 2×SSC, 0.2% SDS at 40° C. for 30 minutes, or
- (c) an amino acid sequence comprising amino acids 20–527 of the sequence of SEQ ID NO: 2.

14. A method for reducing the viscosity of a feed comprising adding to the feed an enzyme having rhamnogalacturonase activity to one or more of soy, pea or rapeseed, or other material derived from Fabales or Cruciferaceae, wherein the enzyme is one of:
- (a) a protein encoded by nucleotides 64–1587 of the DNA sequence of SEQ ID NO: 1;
- (b) a protein encoded by a DNA sequence which hybridizes to the same probe as nucleotides 64–1587 of SEQ ID NO: 1 under conditions of presoaking in 5×SSC and prehybridizing for 1 hour at ~40° C. in a solution of 5×SSC, 5×Denhardt's solution, 50 mM sodium phosphate, pH 6.8, and 50 µg of denatured sonicated calf thymus DNA, followed by hybridization in the same solution supplemented with 50 µCi 32-P-dCTP labeled probe for 18 h at ~40° C., followed by washing three times in 2×SSC, 0.2% SDS at 40° C. for 30 minutes; or
- (c) an aimno acid sequence comprising amino acids 20–527 of the sequence of SEQ ID NO:2.

* * * * *